United States Patent
Hermann et al.

(10) Patent No.: US 10,777,071 B2
(45) Date of Patent: *Sep. 15, 2020

(54) SYSTEMS AND METHODS FOR PATTERN RECOGNITION AND INDIVIDUAL DETECTION

(71) Applicant: Clean Hands Safe Hands LLC, Atlanta, GA (US)

(72) Inventors: Christopher D. Hermann, Atlanta, GA (US); Jeremy D. Jass, Atlanta, GA (US); Lance C. Rigdon, Smyrna, GA (US); Berkley A. Baker, Lawrenceville, GA (US)

(73) Assignee: CLEAN HANDS SAFE HANDS LLC, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/715,113

(22) Filed: Dec. 16, 2019

(65) Prior Publication Data
US 2020/0118416 A1    Apr. 16, 2020

Related U.S. Application Data

(63) Continuation of application No. 16/433,972, filed on Jun. 6, 2019, now Pat. No. 10,540,881, which is a
(Continued)

(51) Int. Cl.
G08B 21/24    (2006.01)
(52) U.S. Cl.
CPC ....... *G08B 21/245* (2013.01); *Y10T 137/8158* (2015.04)

(58) Field of Classification Search
CPC combination set(s) only.
See application file for complete search history.

(56) References Cited

U.S. PATENT DOCUMENTS 5,202,666 A * 4/1993 Knippscheer ............ G08B 7/06
340/541
5,223,182 A * 6/1993 Steiner .................... A61L 9/122
261/26
(Continued)

FOREIGN PATENT DOCUMENTS

| EP | 1216505 B1 | 6/2006 |
|---|---|---|
| KR | 1019940008109 B1 | 9/1994 |
| KR | 219950009364 Y1 | 10/1995 |

OTHER PUBLICATIONS

International Search Report and Written Opinion dated Nov. 6, 2014 mailed in International Application No. PCT/US2014/043278 filed on Jun. 19, 2014.
(Continued)

*Primary Examiner* — Travis R Hunnings
(74) *Attorney, Agent, or Firm* — Morris, Manning & Martin, LLP; Bryan D. Stewart

(57) ABSTRACT

The present systems and methods relate to a hand sanitizer system that includes a proximity detector, a dispensing system and an alarm feature, and is operative to identify potentially high risk hygiene situations corresponding to a person in proximity of the system failing to dispense antiseptic or other solution from the dispenser within a predetermined period of time after moving within a predetermined range of the detector.

18 Claims, 13 Drawing Sheets

Related U.S. Application Data continuation-in-part of application No. 16/291,924, filed on Mar. 4, 2019, now Pat. No. 10,467,884, which is a continuation-in-part of application No. 15/914,241, filed on Mar. 7, 2018, now abandoned, said application No. 16/291,924 is a continuation-in-part of application No. 16/043,607, filed on Jul. 24, 2018, now Pat. No. 10,223,895, which is a continuation-in-part of application No. 15/914,246, filed on Mar. 7, 2018, now abandoned, said application No. 16/043,607 is a continuation-in-part of application No. 15/392,500, filed on Dec. 28, 2016, now Pat. No. 10,032,359, which is a continuation of application No. 14/840,995, filed on Aug. 31, 2015, now Pat. No. 9,564,039, which is a continuation of application No. 13/639,669, filed as application No. PCT/US2011/031571 on Apr. 7, 2011, now Pat. No. 9,123,233.

(60) Provisional application No. 62/681,421, filed on Jun. 6, 2018, provisional application No. 62/681,427, filed on Jun. 6, 2018, provisional application No. 62/468,162, filed on Mar. 7, 2017, provisional application No. 62/468,158, filed on Mar. 7, 2017, provisional application No. 61/321,595, filed on Apr. 7, 2010.

(56) References Cited

U.S. PATENT DOCUMENTS

| Patent/Pub No. | Date | Inventor | Classification |
|---|---|---|---|
| 5,619,188 A * | 4/1997 | Ehlers | G08B 13/08 200/61.62 |
| 5,670,945 A * | 9/1997 | Applonie | E03C 1/055 340/540 |
| 5,695,091 A | 12/1997 | Winings et al. | |
| 5,739,759 A * | 4/1998 | Nakazawa | G08B 3/1025 340/7.62 |
| 6,166,640 A * | 12/2000 | Nishihira | H05B 47/105 340/573.1 |
| 6,325,245 B1 * | 12/2001 | Matthews | A47K 5/12 222/181.1 |
| 7,375,640 B1 * | 5/2008 | Plost | A47K 5/1217 340/500 |
| 7,825,812 B2 * | 11/2010 | Ogrin | G08B 21/245 222/175 |
| 2002/0135486 A1 * | 9/2002 | Brohagen | G08B 21/245 340/573.1 |
| 2002/0150198 A1 | 10/2002 | Thompson | |
| 2002/0175815 A1 * | 11/2002 | Baldwin | H05B 47/105 340/567 |
| 2004/0090333 A1 | 5/2004 | Wildman et al. | |
| 2004/0196612 A1 * | 10/2004 | Kraz | A61N 1/14 361/220 |
| 2005/0242942 A1 * | 11/2005 | Staats | G08B 29/126 340/506 |
| 2007/0121319 A1 * | 5/2007 | Wolf | A01M 1/2083 362/231 |
| 2007/0257803 A1 * | 11/2007 | Munro | G08B 21/245 340/573.1 |
| 2007/0279238 A1 * | 12/2007 | Smith | H03K 17/941 340/686.6 |
| 2008/0103636 A1 | 5/2008 | Glenn et al. | |
| 2008/0131332 A1 | 6/2008 | Nguyen et al. | |
| 2008/0246599 A1 | 10/2008 | Hufton | |
| 2009/0051545 A1 * | 2/2009 | Koblasz | G08B 21/245 340/573.1 |
| 2009/0119142 A1 | 5/2009 | Yenni et al. | |
| 2009/0219131 A1 * | 9/2009 | Barnett | G08B 21/245 340/5.2 |
| 2010/0117836 A1 * | 5/2010 | Seyed Momen | G01S 1/70 340/573.1 |
| 2010/0134296 A1 | 6/2010 | Hwang et al. | |
| 2010/0164728 A1 | 7/2010 | Plost | |
| 2010/0282773 A1 | 11/2010 | Lynn | |
| 2010/0315244 A1 | 12/2010 | Tokhtuev et al. | |
| 2010/0328076 A1 | 12/2010 | Kyle et al. | |
| 2011/0025509 A1 * | 2/2011 | Brow | A47K 5/06 340/573.1 |
| 2011/0063106 A1 | 3/2011 | Snodgrass | |
| 2011/0112696 A1 * | 5/2011 | Yodfat | G16H 40/40 700/283 |
| 2011/0169646 A1 | 7/2011 | Raichman | |
| 2011/0234407 A1 * | 9/2011 | Harris | G08B 21/245 340/573.1 |
| 2011/0291840 A1 | 12/2011 | Pelland et al. | |
| 2011/0310071 A1 * | 12/2011 | Segall | G09G 3/3406 345/207 |
| 2011/0316701 A1 | 12/2011 | Alper et al. | |
| 2012/0218106 A1 | 8/2012 | Zaima et al. | |
| 2012/0316497 A1 | 12/2012 | Deutsch | |
| 2013/0046153 A1 | 2/2013 | Hyde et al. | |
| 2013/0113291 A1 | 5/2013 | Recker et al. | |
| 2013/0122807 A1 | 5/2013 | Tenarvitz et al. | |
| 2013/0250823 A1 | 9/2013 | Gaylard et al. | |
| 2013/0262034 A1 | 10/2013 | Iseri et al. | |
| 2013/0331153 A1 | 12/2013 | Krimstock | |
| 2013/0342349 A1 | 12/2013 | Cruz | |
| 2014/0070950 A1 | 3/2014 | Snodgrass | |
| 2014/0225732 A1 | 8/2014 | Limbert et al. | |
| 2014/0266730 A1 | 9/2014 | Hines et al. | |
| 2014/0361897 A1 | 12/2014 | Smith et al. | |

OTHER PUBLICATIONS

International Search Report dated Dec. 23, 2011 mailed in International Application No. PCT/US2011/031571 filed on Apr. 7, 2011.

* cited by examiner

```
list            p=12F508
#include        <p12F508.inc>
.config _MCLRE_OFF & _CP_OFF & _WDT_OFF &_intRC_OSC
            UDATA
sGPIO       res     1
            res     1
            res     1
            res     1
RCCAL       CODE 0x1FF
            res     1
MAIN  CODE 0x000
            movwf OSCCAL
start
            clrf    GPIO
            clrf    sGPIO
            movlw   b'111101'
            tris    GPIO
waiting
            btfss   GPIO,3
            goto    silenced
            btfsf   GPIO,2
            goto    engaged
            goto    waiting
```

FIG. 5A

```
engaged  movlw
         movwf dc3
dly      movlw 244
         movwf dc2
                dc1
check    btfss  GPIO,
                silenced
dly1     nop
         decfsz dc1
                dly1
dly2     nop
                dc1
                dly2
         decfsz dc2
                check
                dc3
                dly
                alarm
alarm           GPIO
                GPIO
                alarm
         Bcf    GPIO,
                silenced
```

FIG. 5B

```
silenced
        movlw
        movwf dc3
dlw     movlw 244
        movwf dc1
            dc1
dlw1  nop
        decfsz dc1
        goto   dlw1
dlw2  nop
        decfsz dc1
        goto   dlw2
        decfsz dc2
            dlw1
        decfsz dc3
            dlw
            waiting
        END
```

FIG. 5C

SYSTEMS AND METHODS FOR PATTERN RECOGNITION AND INDIVIDUAL DETECTION

CROSS REFERENCE TO RELATED APPLICATIONS

This application is a continuation and claims the benefit of, and priority to, U.S. patent application Ser. No. 16/433,972, filed Jun. 6, 2019, entitled "SYSTEMS AND METHODS FOR PATTERN RECOGNITION AND INDIVIDUAL DETECTION" which:

claims the benefit of and priority to:

U.S. Patent Application No. 62/681,421, filed Jun. 6, 2018, entitled "Systems and Methods for Advanced Workflow Analytics"; and U.S. Patent Application No. 62/681,427, filed Jun. 6, 2018, entitled "Systems and Methods for Real-Time Control of Feedback and Individual Detection"; and is a continuation-in-part of:

U.S. patent application Ser. No. 16/291,924, filed Mar. 4, 2019, entitled "Systems for Monitoring Hand Sanitization," which is a continuation in part of:

U.S. patent application Ser. No. 15/914,241, filed Mar. 7, 2018, entitled "Systems and Methods for Data Analytics to Drive Hand Hygiene Behavior Change," which claims the benefit of and priority to U.S. Patent Application No. 62/468,162, filed Mar. 7, 2017, entitled "Systems and Methods for Data Analytics to Drive Hand Hygiene Behavior Change"; and U.S. patent application Ser. No. 16/043,607, filed Jul. 24, 2018, entitled "Systems for Monitoring Hand Sanitization," now U.S. Pat. No. 10,223,895, which is a continuation in part of:

U.S. patent application Ser. No. 15/914,246, filed Mar. 7, 2018, entitled "Systems and Methods for Real-Time Control of Hand Hygiene Sensors and Adaptable Voice and Detection Control," which claims the benefit of and priority to 62/468,158, filed Mar. 7, 2017, entitled "Systems and Methods for Real-Time Control of Hand Hygiene Sensors and Adaptable Voice and Detection Control"; and U.S. patent application Ser. No. 15/392,500, filed Dec. 28, 2016, entitled "Systems for Monitoring Hand Sanitization", now U.S. Pat. No. 10,032,359, which is a continuation of U.S. patent application Ser. No. 14/840,995, filed Aug. 31, 2015, entitled "Systems for Monitoring Hand Sanitization", now U.S. Pat. No. 9,564,039, which is a continuation of U.S. patent application Ser. No. 13/639,669, filed Oct. 5, 2012, entitled, "Systems for Monitoring Hand Sanitization", now U.S. Pat. No. 9,123,233, which is a National Stage entry of and claims benefit of and priority under 35 U.S.C. § 371 to International Application No. PCT/US2011/031571, entitled, "Systems for Monitoring Hand Sanitization" filed on Apr. 7, 2011, which claims the benefit of and priority under 35 U.S.C. §§ 119, 120 to U.S. Patent Application No. 61/321,595, filed Apr. 7, 2010, entitled, "Systems for Monitoring Hand Sanitization";

all of which are incorporated herein by reference in their entireties.

TECHNICAL FIELD

The disclosure generally relates to sanitization.

BACKGROUND

Approximately 10% of patients who are admitted to hospitals acquire an infection while in the hospital. These infections are typically more serious due to problems with antibiotic resistant strains. These infections not only dramatically increase the cost of care, but more importantly are a cause of substantial morbidity and mortality. The most common method for the spread of nosocomial infections is from direct contact with health care providers' hands. As a result, the CDC has issued recommendations that healthcare providers wash their hands or use an instant hand sanitizer before and after all patient's contacts.

At the present time nearly all hospitals have installed instant hand sanitizer dispensers in all patient rooms and strategically placed signs reminding health care workers to use the dispensers. Despite this improvement, there is at best 50% compliance among health care workers. In most cases the providers are distracted with other responsibilities and simply forget.

Although there are devices designed to monitor sanitization compliance, these devices tend to be impractical in hospital settings, are prohibitively expensive to use on a large scale, and/or would require substantial renovation to implement.

BRIEF SUMMARY

A hand sanitization system is provided that provides notice to a person of proximity to the system and non-compliance with sanitization protocols. In certain embodiments, the system also provides automated monitoring of compliance with sanitation protocols.

Generally, a hand sanitization system is provided that includes a unit housing, a proximity detector mounted to the housing operative to determine proximity of a person with respect to the detector; a dispenser mounted to the housing and being operative to dispense antiseptic solution; and an alarm mounted to the housing and being operative to provide an indication to the person, the indication corresponding to the person failing to dispense antiseptic solution from the dispenser within a predetermined period of time after moving within a predetermined range of the detector. In some embodiments, a hand sanitization system is provided that includes one or more of the above-described dispenser and one or more electronic tags that may be worn by one or more persons and affixed to one or more pieces of equipment. In particular embodiments, the one or more electronic tags may be operative to communicate with one or more dispensers, a central computing system/station, and/or a data collection server, and may transmit information from one or more sensors operatively connected to the one or more electronic tags. In at least one embodiment, the central computing station and/or the data collection server may perform pattern recognition on information received from the one or more tags and the one or more dispensers to determine if a potential high-risk scenario is potentially about to occur, is occurring, or has occurred. In one embodiment, the central computing station and/or the data collection server may be operative to execute one or more pre-programmed responses, following pattern recognition, that modify behavior of the one or more dispensers and or the one or more tags.

According to a first aspect, a hand sanitization system including: A) at least one sanitization unit including: 1) a proximity detector operatively connected to a housing, the proximity detector operative to determine proximity of the person with respect to the at least one sanitization unit; 2) a proximity sensor action counter operatively connected to the proximity detector, the proximity sensor action counter for counting each proximity indication from the proximity detector indicating when the person is within a particular predetermined range; 3) a sanitizer action counter operatively connected to a dispenser attached to the at least one sanitization unit, the sanitizer action counter for counting each time the particular dispenser is activated; 4) an alarm operatively connected to the housing and being operative to provide an indication to the person, the indication corresponding to the person failing to dispense antiseptic solution from the dispenser within a particular predetermined period of time after moving within the predetermined range of the sanitization unit; 5) an alarm counter operatively connected to the alarm, the alarm counter for counting each time the alarm is activated; and 6) a sanitization unit processor operatively connected to memory and a sanitization radio frequency module for communicating with at least one tag and a central computing system; B) the at least one tag including: 1) a tag radio frequency module operative to communicate with the at least one sanitization unit and the central computing system; and 3) one or more sensors for tracking a location of the at least one tag; and C) the central computing system in communication with the at least one sanitization unit and the at least one tag and including at least one centralized processor for receiving an alert notification in response to receiving: 1) an indication from the at least one sanitization unit that the person failed to dispense antiseptic solution from the dispenser within the particular predetermined period of time after moving within the predetermined range of the at least one sanitization unit; and 2) an indication from the least one tag that the at least one tag has moved beyond a predetermined distance from the predetermined range.

According to a second aspect, the hand sanitization system of the first aspect or any other aspect, wherein the one or more sensors for tracking location of the at least one tag includes a GPS sensor.

According to a third aspect, the hand sanitization system of the second aspect or any other aspect, wherein: A) the at least one tag includes an accelerometer; and B) the central computing system determines an approximate speed at which the at least one tag has moved beyond the predetermined distance from the predetermined range.

According to a fourth aspect, the hand sanitization system of the third aspect or any other aspect, wherein: A) the at least one sanitization unit is a first sanitization unit; B) the central computing system is in communication with the first sanitization unit and the at least one tag and including at least one centralized processor for providing an alert in response to receiving: 1) an indication from the first sanitization unit that the person failed to dispense antiseptic solution from the dispenser within the particular predetermined period of time after moving within the predetermined range of the first sanitization unit; 2) an indication from the least one tag that the at least one tag has moved beyond a predetermined distance from the predetermined range, providing an alert notification to the person; and 3) an indication from a second sanitization unit that the person failed to dispense antiseptic solution from a second dispenser attached to the second sanitization unit.

According to a fifth aspect, the hand sanitization system of the fourth aspect or any other aspect, wherein the alert includes a notification to a mobile device associated with the person.

According to a sixth aspect, the hand sanitization system of the fourth aspect or any other aspect, wherein the alert includes a notification to a third-party computing system.

According to a seventh aspect, the hand sanitization system of the fourth aspect or any other aspect, wherein: A) the second sanitization unit includes a second sanitization unit processor operatively connected to memory; B) the second sanitization unit processor is configured for receiving one or more properties via a network; C) the one or more properties modify a behavior of the second sanitization unit; and D) the alert includes the one or more properties for modifying the behavior of the second sanitization unit.

According to an eighth aspect, the hand sanitization system of the seventh aspect or any other aspect, wherein the one or more properties modify the behavior of the second sanitization unit by causing the second sanitization unit to sound an audible alarm.

According to a ninth aspect, the hand sanitization system of the seventh aspect or any other aspect, wherein the one or more properties modify the behavior of the second sanitization unit by causing the second sanitization unit to increase a volume of an audible notification.

According to a tenth aspect, a hand sanitization tracking method including: A) providing an alert notification in response to receiving at a central computing system: 1) an indication that a person failed to dispense antiseptic solution from a dispenser within a particular predetermined period of time after moving within a predetermined range of at least one sanitization unit from a sanitization unit processor operatively connected to memory and a sanitization radio frequency module for communicating with at least one tag and the central computing system, wherein the at least one sanitization unit includes: i) a proximity detector operatively connected to a housing, the proximity detector operative to determine proximity of the person with respect to the at least one sanitization unit; ii) a proximity sensor action counter operatively connected to the proximity detector, the proximity sensor action counter for counting each proximity indication from the proximity detector indicating when the person is within a particular predetermined range; iii) a sanitizer action counter operatively connected to a dispenser attached to the at least one sanitization unit, the sanitizer action counter for counting each time the particular dispenser is activated; iv) an alarm operatively connected to the housing and being operative to provide an indication to the person, the indication corresponding to the person failing to dispense antiseptic solution from the dispenser within a particular predetermined period of time after moving within the predetermined range of the sanitization unit; and v) an alarm counter operatively connected to the alarm, the alarm counter for counting each time the alarm is activated; and 2) an indication that at least one tag has moved beyond a predetermined distance from the predetermined range from a tag radio frequency module operative to communicate with the at least one sanitization unit and the central computing system, wherein the at least one tag includes one or more sensors for tracking a location of the at least one tag.

According to an eleventh aspect, the hand sanitization tracking method of the tenth aspect or any other aspect, wherein the one or more sensors for tracking the location of the at least one tag includes a GPS sensor.

According to a twelfth aspect, the hand sanitization tracking method of the eleventh aspect or any other aspect, wherein: A) the at least one tag includes an accelerometer; and B) the central computing system determines an approximate speed at which the at least one tag has moved beyond the predetermined distance from the predetermined range.

According to a thirteenth aspect, the hand sanitization method of the tenth aspect or any other aspect, wherein: A) the at least one sanitization unit is a first sanitization unit; B) the central computing system is in communication with the first sanitization unit and the at least one tag and including at least one centralized processor for providing an alert in response to receiving: 1) an indication from the first sanitization unit that the person failed to dispense antiseptic solution from the dispenser within the particular predetermined period of time after moving within the predetermined range of the first sanitization unit; 2) an indication from the least one tag that the at least one tag has moved beyond a predetermined distance from the predetermined range, providing an alert notification to the person; and 3) an indication from a second sanitization unit that the person failed to dispense antiseptic solution from a second dispenser attached to the second sanitization unit.

According to a fourteenth aspect, the hand sanitization tracking method of the thirteenth aspect or any other aspect, wherein the alert includes a notification to a mobile device associated with the person.

According to a fifteenth aspect, the hand sanitization tracking method of the thirteenth aspect, wherein the alert includes a notification to a third-party computing system.

According to a sixteenth aspect, the hand sanitization tracking method of the thirteenth aspect or any other aspect, wherein: A) the second sanitization unit includes a second sanitization unit processor operatively connected to memory; B) the second sanitization unit processor is configured for receiving one or more properties via a network; C) the one or more properties modify a behavior of the second sanitization unit; and D) the alert includes the one or more properties for modifying the behavior of the second sanitization unit.

According to a seventeenth aspect, the hand sanitization tracking method of the sixteenth aspect or any other aspect, wherein the one or more properties modify the behavior of the second sanitization unit by causing the second sanitization unit to sound an audible alarm.

According to an eighteenth aspect, the hand sanitization tracking method of the sixteenth aspect or any other aspect, wherein the one or more properties modify the behavior of the second sanitization unit by causing the second sanitization unit to increase a volume of an audible notification.

BRIEF DESCRIPTION OF THE DRAWINGS

Many aspects of the disclosure can be better understood with reference to the following drawings. The components in the drawings are not necessarily to scale. Moreover, in the drawings, like reference numerals designate corresponding parts throughout the several views.

FIG. 5A is an appendix showing one embodiment of programming the microcontroller.

FIG. 5B is an appendix showing one embodiment of programming the microcontroller.

FIG. 5C is an appendix showing one embodiment of programming the microcontroller.

DETAILED DESCRIPTION

Overview

Figure 1:
FIG. 1 is a schematic diagram depicting an exemplary embodiment of a system for monitoring hand sanitization.

Systems for monitoring hand sanitization are provided, several exemplary embodiments of which will be described in detail. In this regard, such a system is designed to improve hand sanitization practices in locations such as hospitals rooms. Notably, the CDC recommends that healthcare providers wash their hands or use an antiseptic hand sanitizer before and after each patient contact. The system is configured to serve as a reminder to providers who enter a patient's room, for example, and forget to use a hand sanitizer. If a provider walks by a system sensor and does not use the sanitizer during a potentially variable time period, an alarm may sound until the provider uses the sanitizer.

In various embodiments, the dispenser stations (including one or more sensors) are installed throughout a hospital and/or patient care rooms and are intended to collect information related to the location of healthcare providers, patients, visitors, or other individuals throughout a facility or room. In at least one embodiment, the dispenser stations are connected by a network to a central computer that can be located at, but not limited to, a nursing station or administration offices. In one embodiment, the dispenser stations can communicate with other dispenser stations directly or through network relays, can communicate through central network coordinators, and can communicate with one or more cloud servers. In one or more embodiments, it is possible that each component of the individual network can make decisions independently as a group, or as subgroups within the network. In further embodiments, the system captures, aggregates, and processes the data from the dispenser stations and/or sensors to identify anomalies or patterns that may indicate that there is a high risk or atypical situation based on one or more pieces of data collected by the sensor or network of sensors. In one or more embodiments, the dispenser stations may receive behavior commands that include various protocols with standardized procedures required by a facility. Examples of behavioral commands include, but are not limited to, *Clostridium difficile* ("C. Diff") protocols, multi resistant drug organisms ("MRDOs") protocols, methicillin-resistant *Staphylococcus aureus* ("MRSA") protocols and/or night shift vs. day shift protocols, each of which, in some embodiments, affect the behavior of a dispenser station, sensor, and/or group of dispenser stations.

As will be understood from discussions herein, a hospital, nursing home, and/or facility deploying the disclosed system and methods may install an array of "SOAP" or "ALCOHOL" dispenser stations throughout the building. In some embodiments, a central computer located at a nursing station (or other location) is operatively connected to a data collection server operatively connected to dispenser station(s). In one or more embodiments, data collected by the dispenser stations/sensors and data stored in the computers/servers is analyzed to identify behavior patterns of interest. These behavior patterns can be identified through a combination of data collected by the dispenser station/sensor network as well as pulled from other data sources (e.g., third party computing systems or the like). According to various embodiments, collected data can be used to identify and predict when potentially dangerous situations may occur and information can be relayed to control dispenser station/sensor behavior based on various protocols.

Various embodiments of the systems and methods presented herein relate to novel algorithms, technology, and processes that may lead to improved sanitation compliance. More specifically, various embodiments of the systems and methods relate to the use of data patterns to drive particular patterns of behavior for purposes including, but not limited to, identifying and/or responding to trends, phenomena, changes, etc. in hand hygiene behavior.

Exemplary Embodiments

An exemplary embodiment of a system for monitoring hand sanitization is depicted schematically in FIG. 1. As shown in FIG. 1, the system (10) includes a proximity detector (12), a dispenser (14) and an alarm (16). The proximity detector determines proximity of a person with respect to the detector. In some embodiments, the proximity detector includes an infrared range finder and a variable potentiometer operative to adjust range sensitivity of the range finder. In some embodiments, the proximity detector is a single, non-directional sensor which detects proximity of a body to the sensor rather than movement of a body in front of the system. The dispenser typically dispenses antiseptic solution, which can be an alcohol-based solution or can be of any other type of sanitizing gel or solution, and provides an output signal to the system corresponding to dispensing of the antiseptic solution. The alarm is operative to provide an indication when there is a failure to dispense based on input criterion. In specific embodiments, the alarm sounds when the person fails to dispense antiseptic solution from the dispenser within a predetermined period of time after moving within a predetermined range of the detector. In some embodiments, the indication can be visual and/or audible. In some embodiments, the period of time is from between 1 second to about 1 minute, or between about 5 seconds and about 45 seconds, or about 10 seconds to about 30 seconds, or is set to at least 1, at least 2, at least 3, at least 4, at least 5, at least 10, at least 15, at least 20 or at least 30 seconds.

Figure 2:
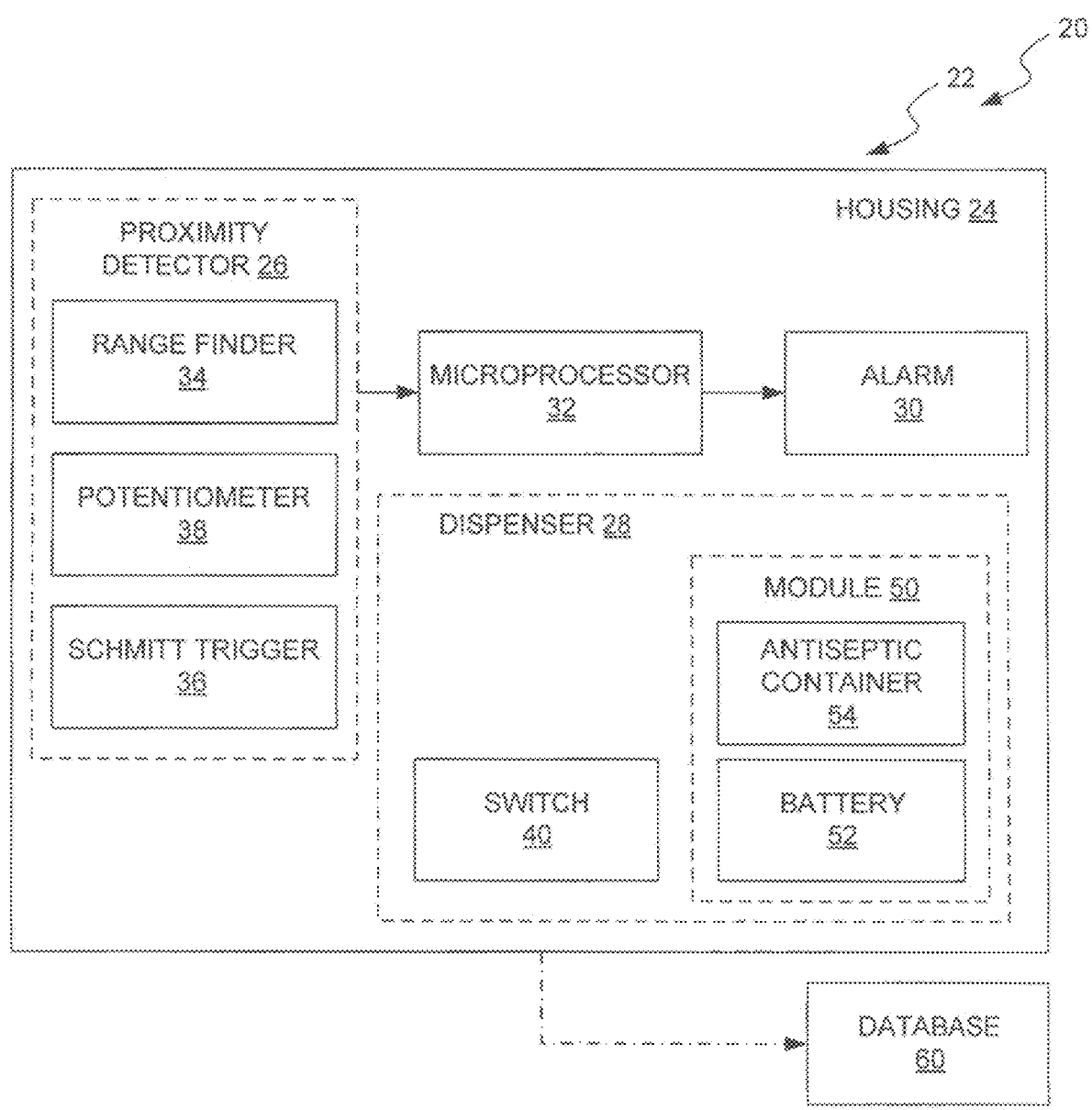
FIG. 2 is a schematic diagram depicting another exemplary embodiment of a system for monitoring hand sanitization.

Another exemplary embodiment of a system for monitoring hand sanitization is depicted schematically in FIG. 2. As shown in FIG. 2, the system 20 includes a sanitization unit 22 incorporating a housing 24, a proximity detector 26, a dispenser 28, an alarm 30 and a microprocessor 32, a switch/usage sensor 40, a radio, memory, an LED, a radio frequency chip (RF), a power source, and one or more optional mechanical switches. It should be noted that these components of the dispenser station are merely exemplary. Dispenser station may include any number of additional components not shown and may function with any number of the components shown removed, as will be understood by one of ordinary skill in the art. It should be understood that each dispenser station may be operatively connected to a mesh network (as further described herein) and may be assigned a particular unique identifier. In various embodiments, each dispenser station may be operatively connected to but not limited to a star, fully connected, or tree network.

In a particular embodiment, the dispenser station is added on to an existing housing and dispenser (e.g., the housing and dispenser are attached to the dispensing station; the dispensing station comes in various connected components that are operatively attached to the housing and/or dispenser, etc.). In further embodiments, the dispensing station includes the dispenser and housing as part of the design (e.g., the dispensing station is not an add-on, but is integrated with the dispenser and housing).

It should also be understood that that a dispenser station (and dispenser and housing) may include, store, and dispense any suitable type of hand hygiene solution and/or product. In various embodiments, the hand hygiene product is soap. In some embodiments, the hand hygiene product is a particular type of soap, such as anti-bacterial soap. In further embodiments, the hand hygiene product is hand sanitizer or hand antiseptic (e.g., any commonly (or uncommonly) produced gel, foam, or liquid with an anti-microorganism substance, typically alcohol).

In various embodiments, the proximity detector/sensor 26 is mounted to the housing and determines proximity of a person with respect to the detector/sensor 26. In at least one embodiment, the dispenser station is mounted to the housing and dispenses antiseptic solution. In one or more embodiments, the alarm is mounted to the housing and provides an indication to a person. By way of example, an alarm/indication may correspond to the person failing to dispense antiseptic solution from the dispenser within a predetermined period of time after moving within a predetermined range of the detector. In some embodiments, the microprocessor 32 receives input from the proximity detector and from the dispenser and provides an output to the alarm based, at least in part, on the inputs received.

Figure 3:
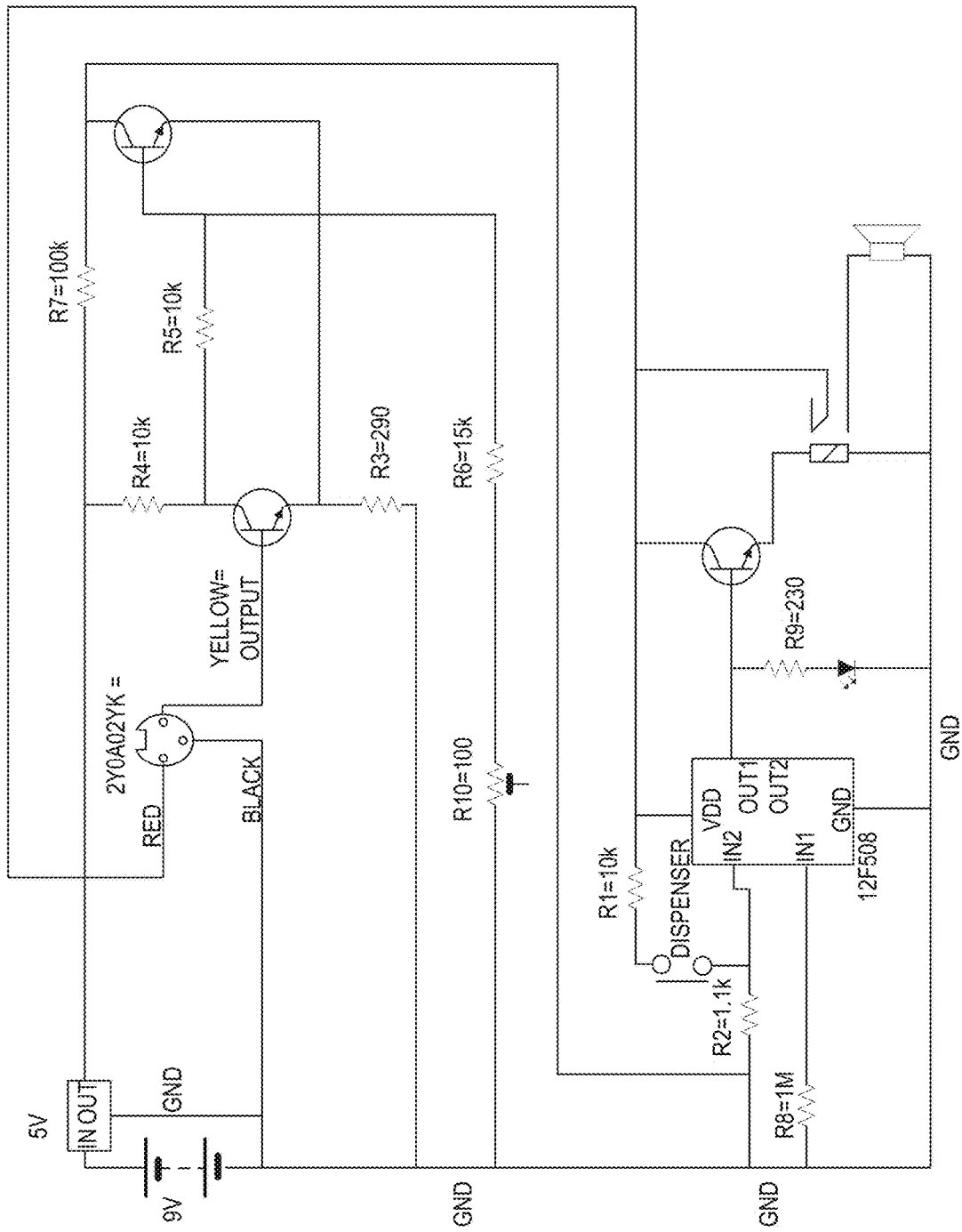
FIG. 3 is a circuit diagram related to another exemplary embodiment of a system for monitoring hand sanitization.

In the embodiment shown in FIG. 2, the proximity detector/sensor 26 includes an infrared (IR) range finder 34, a Schmitt trigger 36 and a potentiometer 38 (also shown in FIG. 3). In some embodiments, the proximity detector relays a signal to the microprocessor that triggers an alarm if an object enters a predetermined field without actuating the dispenser. In at least one embodiment, a proximity detector/sensor 26 is operatively connected to one or more processors (e.g., microprocessor 32). The proximity sensor 26 may be any suitable proximity sensor discussed herein, including, but not limited to an ultrasound sensor, laser sensor, optical/light sensor, heat sensor, radar sensor, sensor that utilizes Wi-Fi, radio waves, etc. The proximity sensor 26 may be configured to receive an indication of a particular object within a predetermined range depending on the type of sensor (e.g., an ultra sound sensor receives sound, etc.). It should be understood that proximity sensor 32 may represent multiple sensors (e.g., multiple ultrasound sensors, etc.).

In at least one embodiment, the proximity detector/sensor 26 may be adjustable. In various embodiments, the proximity sensor 26 is adjustable by a mechanical or digital switch (e.g., one or more mechanical switches). In one or more embodiments, proximity sensor 26 is adjustable via programming received from a data communication server (e.g., data communications server 602), from a website, from a web application, and/or from any other suitable source. It should be understood that proximity sensor 26 may be adjustable in any suitable way, including, but not limited to, adjustable in range (e.g., distance and width of field) and/or adjustable in direction.

A representative example of a range finder is a Sharp GP2Y0A02YK infrared range finder, the output of which is processed to serve as a digital input signal to the microprocessor. The range finder is a self-contained transmitter and receiver that are set parallel to each other. If an object enters the detection field, the IR light that is transmitted is reflected to the detector. The closer an object is to the range finder, the more light is reflected, and the higher the output voltage. This exemplary detector has a range between 20-150 cm and when supplied with a 5V produces a voltage of 0.25-2.3 V depending on the distance.

The output is then converted to a digital signal with the Schmitt trigger. Notably, a Schmitt trigger is a bistable multivibrator that either produces a high or low signal depending on the input signal. The Schmitt trigger use two PNP transistors and a series of five resistors that when combined produce either a high or low voltage. If the input exceeds the $V_{on}$ value, the output from the trigger is high or $V_{cc}$. The value for $V_{on}$ is:

$$Von = \left(\frac{R6 + R10}{R4 + R5 + R6 + R10}\right) Vcc$$

If the input drops below $V_{off}$, the output from the trigger is low or ground. The value for $V_{off}$ is:

$$Voff = \frac{(R6 + R10)\left(Vcc + \frac{R4}{R3}.07Vcc\right)}{R4 + R5 + (R6 + R10) + \frac{R4(R6 + R10)}{R3}}$$

A variable potentiometer 38 is used in some embodiments to adjust an effective range of the detector. In the representative circuit of FIG. 3, R10 is a 100Ω potentiometer that when varied changes both the $V_{on}$ and the $V_{off}$. By adjusting the voltage at which the trigger is switched, the potentiometer can vary the distance at which the proximity detector produces a high output voltage.

In some embodiments, the system includes a dispenser switch/usage sensor 40. In various embodiments, the usage sensor 40 is configured to detect one or more actions performed by a user to activate the hand hygiene product dispenser. It should be understood that the usage sensor 40 may be any suitable sensor to detect the action performed by the user to dispense the hand hygiene product. In various embodiments, the usage sensor 40 is a mechanical sensor that detects when the lever of an existing dispenser is pulled (e.g., to dispense the hand hygiene product). In particular embodiments, the usage sensor 40 is configured to detect when the user waves or places their hand in front of a light or motion sensor to indicate they wish the dispenser to dispense the hand hygiene product. It should be understood that in embodiments where the dispenser and/or housing are an integral part of the dispenser station, the usage sensor 40 may be the same sensor used to detect that the user wishes the dispenser to dispense the hand hygiene product.

A representative microprocessor is a Microchip 12F508 microcontroller. In some embodiments, the microcontroller takes inputs from both the Schmitt trigger and dispenser switch 40. In at least one embodiment, the dispenser switch is connected to the hand sanitizer dispenser and closing this switch represents using the sanitizer. In at least one embodiment, based on the two inputs, the microcontroller can in turn activate the alarm. The microcontroller in this embodiment (and others) is programmed (such as shown in the attached FIG. 5) so that if there is a high signal from the Schmitt trigger (corresponding to someone walking in front of the sensor) and the dispenser switch is not closed (indicating that the sanitizer from the dispenser is not used), the alarm will sound until the dispenser switch is closed (indicating that the sanitizer has been used).

In this embodiment (and others), there is a delay built into the program so that there is a three second delay between the time the Schmitt trigger is activated and the sounding of the alarm. This delay is incorporated so that the health care provider has adequate time to use the sanitizer before the alarm sounds. In at least one embodiment, once the dispenser switch is closed, there is a ten second period in which the alarm is silenced. In some embodiments, this delay ensures that the alarm will not sound if the external switch is closed before or while the individual crosses in front of the sensor. Clearly, various delays can be implemented in other embodiments.

Additional features to the circuitry that could be easily added are a photo resistor and a low battery indicator. The low battery indicator could be made with a second Schmitt trigger that could be incorporated or provide input to the microcontroller so that if the battery dropped below a certain voltage (i.e. a low battery) a visual and/or audible alarm could be triggered.

In at least one embodiment, the photo-resistor is a variable resistor that changes voltage based on the light that strikes the surface. This could be incorporated to detect the background light in the patient's room. This would enable the detection of whether the lights are off (i.e. a sleeping patient), and result in either a silenced or reduced volume of the audible alarm, so as not to disturb the patient.

The audible alarm can be a customizable audio recording (or other alarm). In one or more embodiments, the recording is a voice message reminding the healthcare provider to use the hand sanitizer in the event that the user fails to do so while entering or exiting the room. In various embodiments, the combination audio recording chip and microcontroller has the ability to play multiple recordings at varying volumes. In one or more embodiments, the multiple recordings can be used to play randomly selected messages to reduce the potential of conditioning of the providers. Additionally, in some embodiments, multiple recording could be played sequentially in the event that a provider fails to respond to the first message. In further embodiments, the volume of the device could be adjusted based on the ambient light in the room (day/night) or could be varied based on the provider's response.

In one embodiment, a representative audible alarm is a piezo-electric buzzer. In some embodiments, a speaker and driver can be used, among others. The microcontroller could be programmed to emit a variety of tones/buzzers or could be programmed to play a recorded message asking the healthcare provider to use the antiseptic solution. The microcontroller could also be programmed with several tones/ recording as to vary the message played. This could help reduce conditioning of the health care providers resulting in them ignoring the system message.

Another feature that is included in certain embodiments is a modular antiseptic and battery pack (50 in FIG. 2). This modular pack would contain a battery 52 and a container 54 of the antiseptic solution to allow easy replacement by healthcare workers. This would simplify replacing both parts. In addition, the module could provide a continual revenue source for the company supplying the device. The modular battery/antiseptic container could also be made refillable/rechargeable to both save money and be environmentally friendly. There could be a centralized filling station that could automatically recharge the battery and also re-fill the dispenser at the same time.

In various embodiments, the system may include an RF chip. In particular embodiments, RF chip communicates with one or more tags (or other components of the system). It should be understood that RF chip may communicate with one or more tags or other components in any suitable way, including, but not limited to, via Bluetooth, low energy Bluetooth, microwaves, Wi-Fi, radio waves, sonar, etc. As discussed above, RF chip may be an integral part of a system-on-a-chip type system. In one embodiment, RF chip and radio are the same device.

One or more processors (e.g., microprocessor 32) may be operatively coupled to a power source. As will be understood by one of ordinary skill in the art, the power source may be any suitable power source such as a battery and/or outlet type electrical source. It should be understood that the power source may be rechargeable by solar energy (via one or more solar panels not shown) and/or via kinetic energy (e.g., the system is configured to harvest energy each time a user pulls a lever to receive hand hygiene product).

The dispenser station 20 may include one or more mechanical switches operatively connected to one or more processors. One or more mechanical switches may include, for example, an on/off switch for the dispenser station, a calibration/adjustment button/switch for proximity detector/sensor 26, a speaker (not shown), and/or a switch to calibrate and/or adjust an audio message played and/or the speaker volume (including turning the speaker off).

It should be understood that, the dispenser station 20 may be integrated with various other systems such as a security system, a hospital EHR system, a hospital census system, human resource systems, payroll systems, medical supply systems, security door databases, etc.

Additionally or alternatively, some embodiments can incorporate a solar cell for providing power to one or more of the electronic components of the system. By way of example, a solar cell (or array of cells) can be mounted to the housing and used to recharge the system battery, such as when the lights are turned on in the room in which the housing is located.

Figure 4:
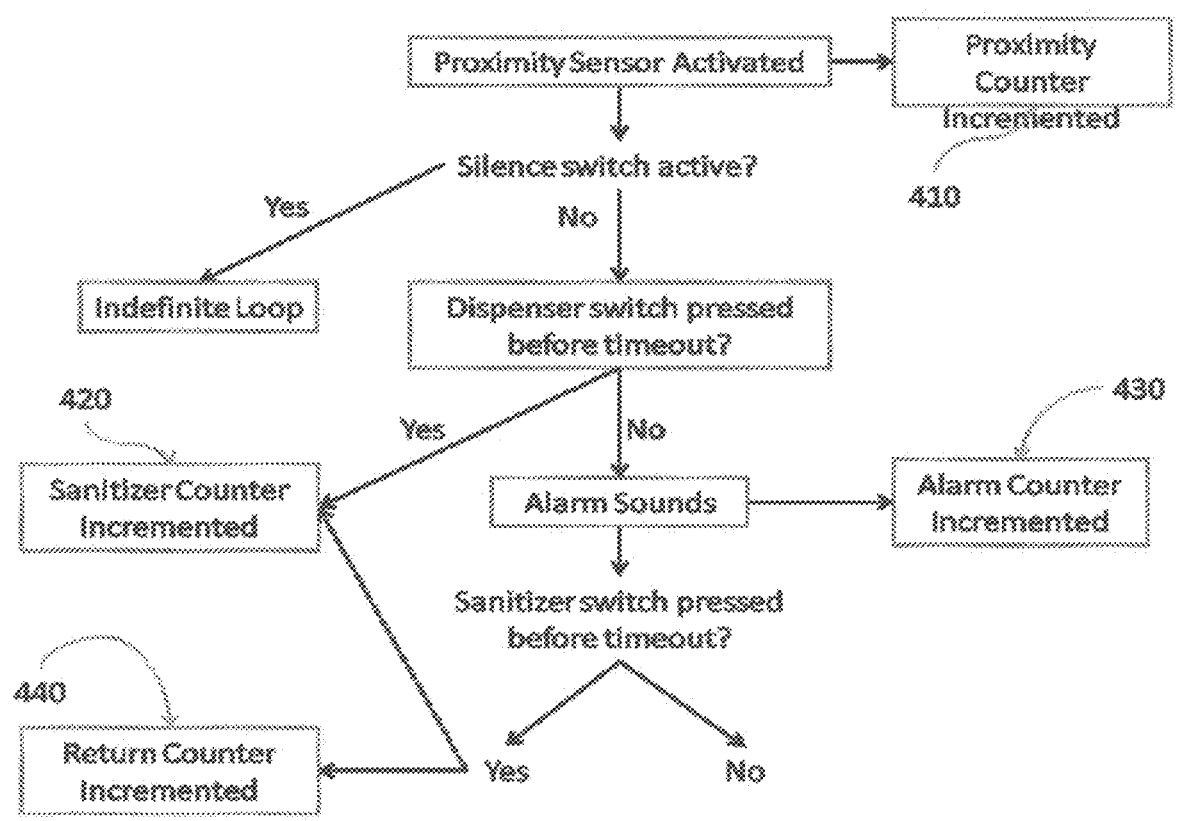
FIG. 4 is a diagram showing an exemplary detection and monitoring sequence.

The device has the ability to track the compliance of all the devices. An exemplary monitoring scheme is shown in FIG. 4. A counter is included to monitor the activation of the Proximity sensor. The proximity sensor action counter 410 can be a physical counter attached directly to the device or can be a remote program or database activated by the activation of the sensor through a wireless network. If the Dispenser dispenses, measured in this embodiment by a dispenser switch (FIG. 2, 40), then another counter 420 is used to identify if the sanitizer switch is pressed before the alarm is activated. As noted above, the period between the proximity sensor activation and alarm is set into the system. If the alarm sounds, a third counter 430 can be used to count the alarm activation. In some embodiments, a fourth "return" sensor 440 is included to identify the activation of the dispenser switch after activation of the alarm. In other embodiments, the system only provides total proximity sensor events and total dispenser activation. In other embodiments, the total alarms are included.

To better monitor the compliance/usage of the sanitizer, data associated with such use could be stored and/or transmitted to another computer/device for recording (such as in a FIG. 2, 60). In some embodiments, the microcontroller is programmed to count the number of times an individual walks past the device, the number of times the antiseptic is dispensed, and also the number of times the alarm sounds. It can also record the number of times that the alarm sounds and a provider returns to use the sanitizer. These numbers can be stored in the device and displayed sequentially on a LED display.

This information could also be transmitted to a second device (either through a wired or wireless device) that could be used to analyze handwashing compliance. At the present time there is no hand sanitizer monitoring device that is widely used in hospitals. The hand sanitizing practices consist of dispensers that are strategically placed and signs reminding health care workers to use them. Even with these improvements the best compliance rates are just approaching 50%. The current compliance tracking requirements are based on tracking aggregate compliance and not individual provider compliance.

An advantage of certain embodiments described herein is active reminders to health care providers to use hand sanitizer. In various embodiments, the system essentially ensures that anyone who walks into or out of a patient room will use the sanitizer. In some embodiments, if a person does not use the sanitizer, an alarm will activate until the sanitizer or the silence button is pressed. There have been other devices that are designed to monitor compliance, but they tend to be impractical in hospital settings, are prohibitively expensive to use on a large scale, or would require substantial renovation to implement them. This system potentially avoids these issues in that it can be stand alone, and very low cost when compared to other devices.

There are certain instances, such as during a code or withdrawal, where it is not appropriate to monitor compliance or play the audio recording. In some embodiments, the device has a switch that can silence the alarm or deactivate the compliance tracking for a predetermined or indefinite period of time.

One of the most important applications for this device is to reduce the incidence and mortality from hospital acquired infections. Roughly 2 million patients per year acquire infections while in the hospital, resulting in approximately 80,000 deaths per year. The most common route of spread is direct contact with health care workers and the commonly accepted solution is to improve hand sanitization practices. In the U.S., there is nearly $6 billion per year spent on treating nosocomial infections, most of which is paid directly by the hospital. According to the American Hospital Association there are roughly 950,000 hospital beds in the U.S., meaning that over $6300 dollars is spent per year just to treat infections acquired while in the hospital. It is estimated that it would cost $250,000 per year (in a 250 bed hospital) for an infection control program that has only achieved a 50% compliance rate in the best of circumstances. This roughly gives a cost of $1000 per bed in each hospital for an infection control program. Multiplying this by the 950,000 beds in the U.S., given an estimate of $950 million dollars per year spent on hospital infection programs.

Various functionality, such as that described above in the flowcharts, can be implemented in hardware and/or software. In the terms of hardware architecture, such a computing device can include a processor, memory, and one or more input and/or output (I/O) device interface(s) that are communicatively coupled via a local interface. The local interface can include, for example but not limited to, one or more buses and/or other wired or wireless connections. The local interface may have additional elements, which are omitted for simplicity, such as controllers, buffers (caches), drivers, repeaters, and receivers to enable communications. Further, the local interface may include address, control, and/or data connections to enable appropriate communications among the aforementioned components.

The processor may be a hardware device for executing software, particularly software stored in memory. The processor can be a custom made or commercially available processor, a central processing unit (CPU), an auxiliary processor among several processors associated with the computing device, a semiconductor based microprocessor (in the form of a microchip or chip set) or generally any device for executing software instructions.

The memory can include any one or combination of volatile memory elements (e.g., random access memory (RAM, such a DRAM, SRAM, SDRAM, VRAM, etc.)) and/or nonvolatile memory elements (e.g., ROM, hard drive, tape, CD-ROM, etc.). Moreover, the memory may incorporate electronic, magnetic, optical, and/or other types of storage media. Note that the memory can also have a distributed architecture, where various components are situated remotely from one another, but can be accessed by the processor.

The software in the memory may include one or more separate programs, each of which includes an ordered listing of executable instructions for implementing logical functions. A system component embodied as software may also be construed as a source program, executable program (object code), script, or any other entity comprising a set of instructions to be performed. When constructed as a source program, the program is translated via a compiler, assembler, interpreter, or the like, which may or may not be included within the memory.

The Input/Output devices that may be coupled to system I/O Interface(s) may include input devices, for example but not limited to, a keyboard, mouse, scanner, microphone, camera, proximity device, etc. Further, the Input/Output devices may also include output devices, for example but not limited to, a printer, display, etc. Finally, the Input/Output devices may further include devices that communicate both as inputs and outputs, for instance but not limited to, a modulator/demodulator (modem; for accessing another device, system, or network), a radio frequency (RF) or other transceiver, a telephonic interface, a bridge, a router, etc.

When the computing device is in operation, the processor can be configured to execute software stored within the memory, to communicate data to and from the memory, and to generally control operations of the computing device pursuant to the software. Software in memory, in whole or in part, is read by the processor, perhaps buffered within the processor, and then executed.

Figure 6:
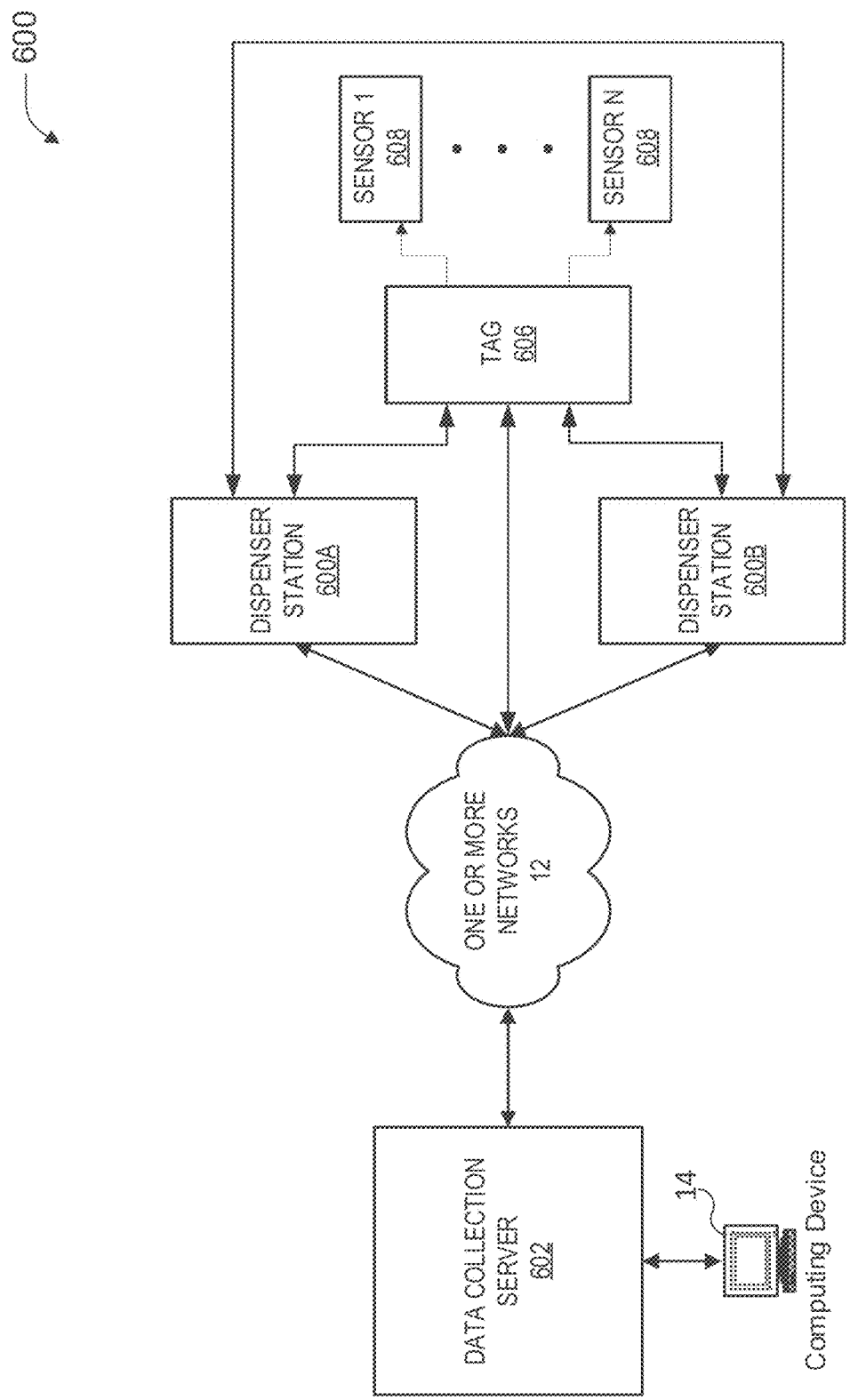
FIG. 6 is an illustration of a high-level exemplary architecture of a system for monitoring hand sanitization, according to one embodiment of the present disclosure.

FIG. 6 depicts a high-level exemplary architecture 600 of various systems and methods disclosed herein. As shown in the embodiment in FIG. 6, the system includes a computing device 14 operatively connected to a data collection server 602 (e.g., database 60 as shown in FIG. 2). Data collection server 602 is, in the embodiment shown, operatively connected to dispenser station 600A and 600B via one or more networks 12. Dispenser station 600A is operatively connected to dispenser station 600B. Dispenser station 600B is operatively connected to dispenser station 600A. Dispenser stations 600A and 600B are merely exemplary. It will be understood by one of ordinary skill in the art that the system may include any number of networks, dispenser stations, tags, data collections servers, and/or computing devices that may be operatively connected to one another (or to specific components of the system). In one embodiment, the system may further include one or more tags configured to communicate with the dispenser stations 600A and 600B and/or the data collection server 602.

In the embodiment shown in FIG. 6, the system further includes at least one tag 606. In at least one embodiment, the tag 606 refers to any tag, described herein, that is attached to a provider, or, in some embodiments, hospital or other equipment (for example, beds). As further described herein, the tag 606 may include components (such as an RF chip) for transmitting and receiving communications to and from the data collection server 602 (e.g., via one or more networks 12), dispenser stations 600A and 600B, and various other components. In various embodiments, the system may include a multitude of tags 606 that may communicate with any number of dispenser stations. In one or more embodiments, the tag 606 may be connected to one or more sensors 608 (e.g., illustrated as 1 to n sensors in FIG. 6). In various embodiments, the one or more sensors 608 may include, but are not limited to: 1) one or more accelerometers; 2) one or more gyroscopes; 3) one or more tilt sensors; 4) one or more vibration sensors; 5) one or more GPS sensors; and 6) one or more other sensors. In some embodiments, the one or more sensors 608 may be housed together with the at least one tag 606. In at least one embodiment, the at least one tag 606 includes a processor that receives data from the one or more sensors 608 and transmits the data to one or more system components (e.g., dispenser stations 600 A/B, a data collection server 602, a central computing station, etc.).

In general, in the exemplary embodiment of FIG. 6, each of the devices shown are in operative communication with various other devices. It should be understood, and will be further discussed herein, that various components may be operatively connected in ways not shown in FIG. 6. Additionally, although only one or more networks 12 are shown, it will be understood that the system may include any number of suitable networks, which may be, for example, wireless networks, directly connected (e.g., wired), Bluetooth, mesh networks, or any other suitable type of network.

Exemplary Environment

Figure 7:
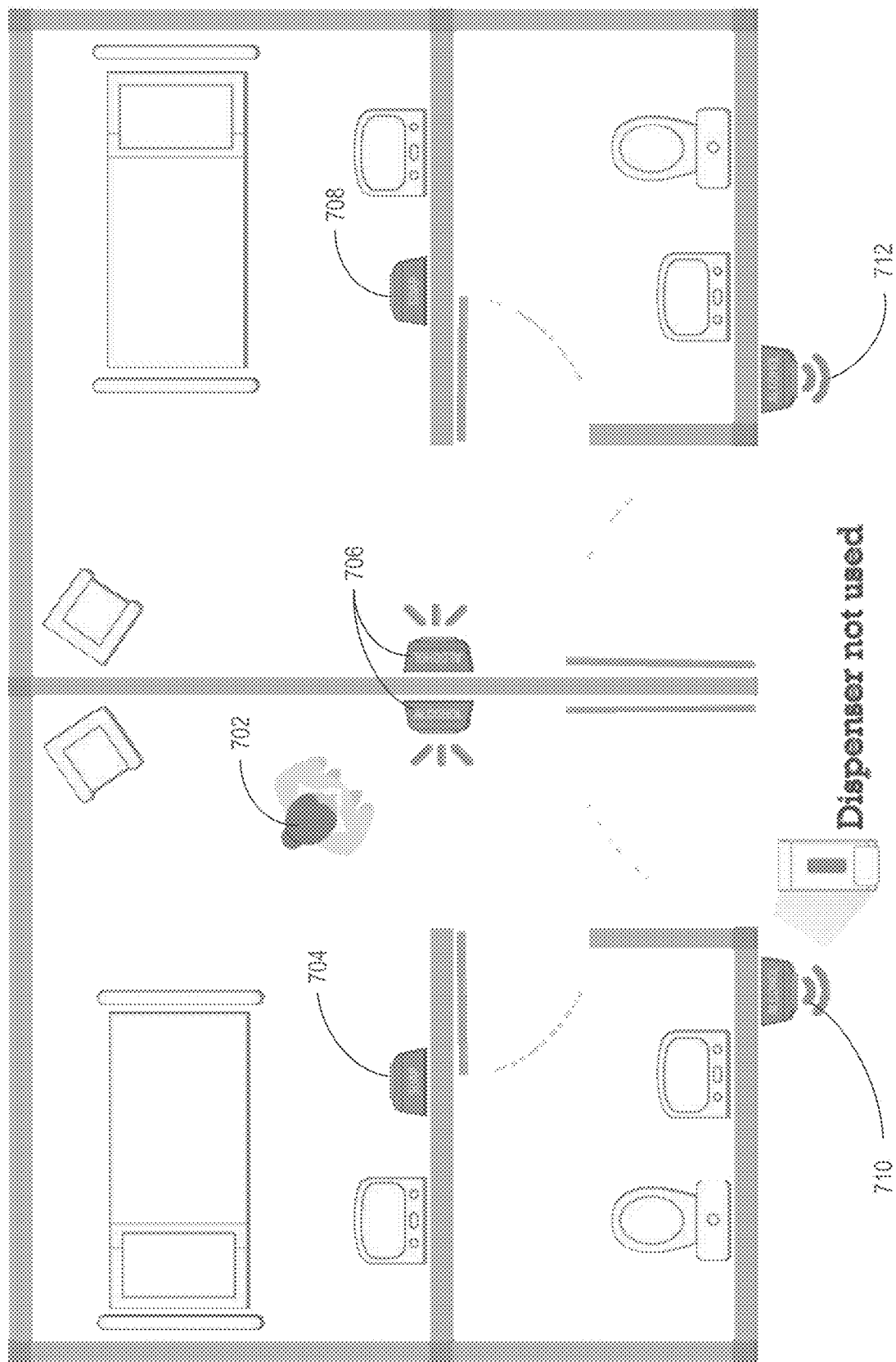
FIG. 7 is an illustration of an exemplary system environment, according to one embodiment of the present disclosure.

As discussed above, various aspects of the present systems and methods relate to identifying an individual across multiple dispenser stations. FIG. 7 shows an exemplary system environment with an exemplary individual 702 and six exemplary networked dispenser stations 704-712 in operative communication. As shown in this exemplary embodiment, dispenser stations 704 and 708 are "SOAP" stations (e.g., dispenser stations for dispensing soap as a hand hygiene product) and dispenser stations 706, 710, and 712 are "ALCOHOL" stations (e.g., dispenser stations for dispensing an alcohol-based hand hygiene product).

In the embodiment shown, dispenser station 710 detected individual 702 go past the dispenser via one or more proximity sensors without using the hand hygiene product (e.g., the individual 702 did not perform the action to dispense the hand hygiene product). Dispenser station 710 sends, via one or more radios, an indication that individual 702 walked past dispenser station 710 without using the hand sanitizer. Upon receiving this indication, dispenser station 706 plays an audio message reminding individual 702 to use the hand hygiene product.

It should be understood from FIG. 7 and various discussions herein that the system may be configured to identify the range between an individual and a dispenser station, therefore detecting when an individual enters or exits a patient's room.

In various embodiments where more than one dispenser station is networked (e.g., as shown in FIG. 7), the system may coordinate between multiple dispenser stations placed in various locations (e.g., throughout a hospital). One example, would be communication between a dispenser station inside and a dispenser station outside a patient's room to allow a provider to use either the sanitizer inside or outside the room and still receive credit for a successful patient interaction (e.g., the system logs that the individual used the dispenser station according to protocol).

Exemplary Processes

Figure 8:
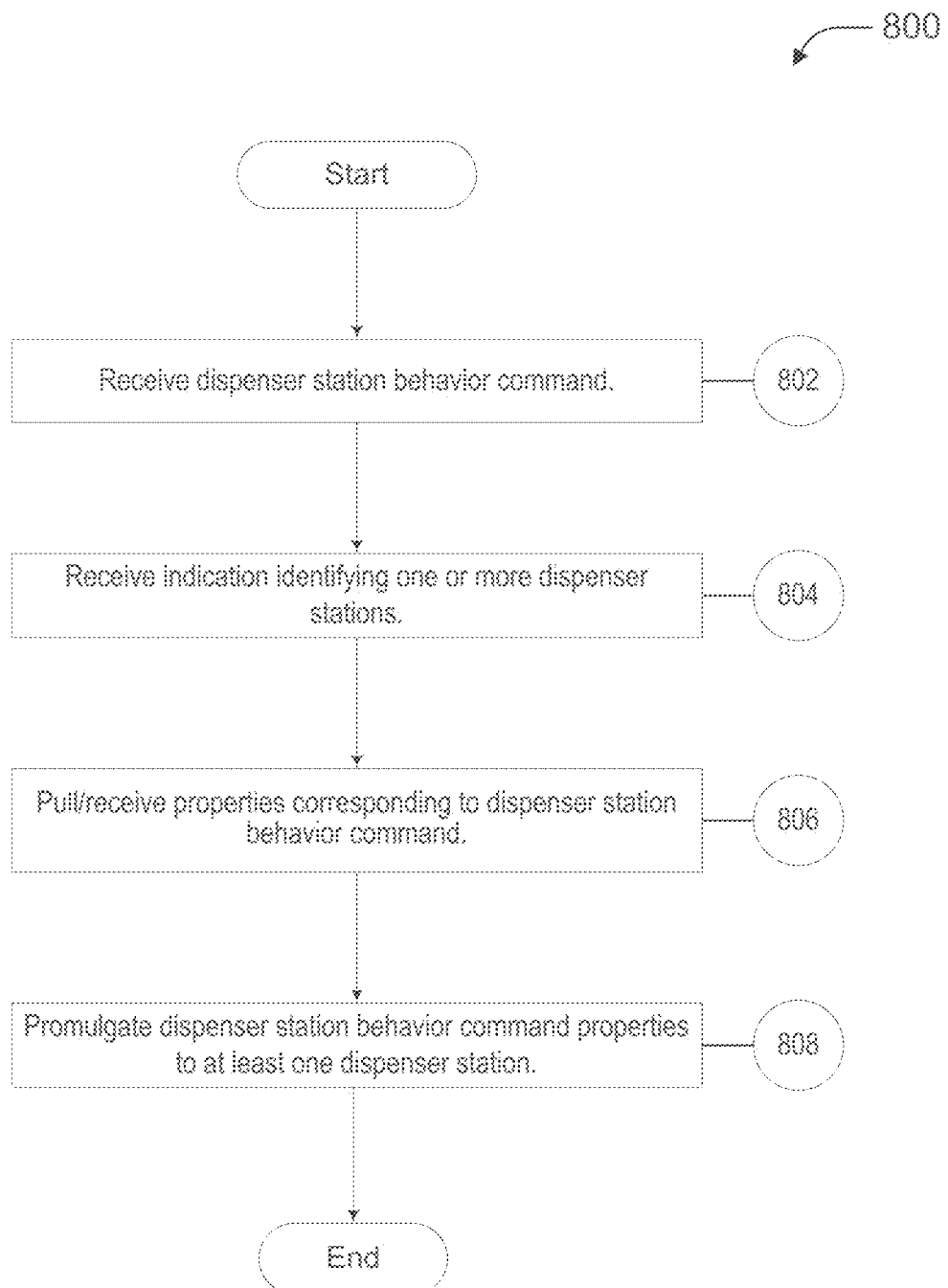
FIG. 8 is an exemplary flowchart illustrating an exemplary behavior command selection and promulgation process, according to one embodiment of the present disclosure.

Turning now to FIG. 8, an exemplary flowchart illustrating an exemplary dispenser behavior command process is shown, according to one embodiment. The process begins at step 802, where the system receives one or more dispenser station behavior command(s). In one or more embodiments, the system receives the one or more dispenser station behavior commands via a drop-down box or other suitable input at a central computing system (e.g., data collection server 602 or the like). In at least one embodiment, the system receives the one or more dispenser station behavior commands by voice command. In some embodiments, the system receives the one or more dispenser station behavior commands from another computing system (e.g., another computing system within a hospital system). In further embodiments, the system receives the one or more dispenser station behavior commands based on electronic medical records of a particular patient (e.g., the patient has a particular condition, such as C. Diff or the like and the system creates/receives behavior commands based on this condition).

In some embodiments, the one or more behavior commands are protocols for changing and/or updating functionality of one or more dispenser stations (e.g., a single dispenser station, all dispenser stations, or a subgroup or subgroups of dispenser stations). As will be understood from discussions herein, in one embodiment, the behavior commands may fully update a dispenser station's firmware. In various embodiments, the behavior commands may make temporary changes to a current configuration state of a dispenser station, but not completely reprogram the dispenser station.

As further discussed herein, the one or more behavior commands are various protocols related to particular situations, circumstances, etc. Examples of behavior commands include, but are not limited to, protocols in the event of a C. Diff, MRDO and/or MRSA outbreak or protocol procedures regarding a health care provider's interaction with a patient (e.g., during a night vs. day shift). For example, a behavior command related to C. Diff may include protocols and/or programming transmitted to one or more dispenser stations outside of a patient's room that is infected with C. Diff. Continuing with this example, the behavior command may change the programming of the one of more dispensers from a reminder to use hand sanitizer to a reminder/warning not to enter the C. Diff-infected patient's room.

For example, a nurse might manually enter or electronically receive data indicating that a patient has C. Diff. The nurse can select the C. Diff protocol that is stored in the data collection server from a menu driven user interface wherein choices can be selected on the computing device. The system receives an indication to identify the dispenser station within the C. Diff-infected patient's room and the behavior command can modify dispenser behavior to an output that alerts the health professional to use soap instead of alcohol.

In one embodiment, additional patient factors may include but are not limited to, isolation status of a patient, suspected infection of the patient, patient infection or colonization status, patient medical history and risk factors, patients in nearby rooms/units, which staff takes care of specific patients and the risk factors of those patients, status of factors that pose risks to patients (e.g. central lines, catheters, ventilators, post-op surgical status, etc.).

At step 804, the system receives an indication identifying one or more dispenser stations (e.g., the dispenser station or group of dispenser stations that are to receive a behavior commend). In various embodiments, the system receives the indication identifying the one or more dispenser stations via input to the central computing system. In some embodiments, the system is configured to retrieve the indication identifying the one or more dispenser stations from memory (e.g., one or more dispenser stations may be associated with a particular behavior command in memory such that when the particular behavior command is received/selected/etc., the system is configured to retrieve the corresponding indication of the one or more dispenser stations from memory). In a particular embodiment, the system receives the indication identifying the one or more dispenser stations via another computing system, such as, for example, a third-party computing system, a cell phone, a mobile application, and/or another computing system at a hospital, clinic, or the like. In further embodiments, the system receives the indication identifying the one or more dispenser stations via one or more dispenser stations (e.g., a dispenser station or group of dispenser stations indicates one or more dispenser stations that should receive a behavior command).

As will be understood from discussions herein, dispenser stations may be identified by serial number, device number, or the like and may be "grouped" based on type (e.g., soap vs. alcohol-based solution), location (e.g., all dispenser stations near a particular patient's room), floor, etc. In various embodiments, groups or subgroups of dispensers stations are associated with a particular identifier. In these embodiments (and others), the system receives a behavior command at step 802 and receives the particular identifier associated with the group of dispenser stations such that the system can promulgate properties associated with the behavior command (further discussed below) to the dispenser stations associated with the particular identifier.

The identifier may be any suitable identifier such as a number, label (e.g., "FLOOR 11 DISPENSERS"), or the like.

At step 806, the system pulls and/or receives properties corresponding to the received dispenser station behavior command(s). In various embodiments, in response to receiving the dispenser station behavior command(s) and/or the indication identifying the one or more dispenser stations, the system is configured to pull properties from memory (e.g., from a local, remote, or distributed database or databases) corresponding to the dispenser station behavior commands to send to the one or more dispenser stations. In particular embodiments, the system is configured to receive the corresponding properties from a third-party system (e.g., in response to transmitting the dispenser station behavior commands to the third-party system).

In various embodiments, the properties corresponding to the dispenser station behavior commends include one or more changes to a dispenser station component and/or functionality. For example, a property may correspond to (a command or commands for) changing a volume of a dispenser station reminder. As another example, a property may correspond to changing an audio reminder of a dispenser station (e.g., from a voice reminder to use hand sanitizer to a voice reminder to use soap). As yet another example, a property may correspond to activating a light sensor to determine whether it is evening/night and a second property may correspond to lowering a volume of a reminder based on data received from the light sensor (e.g., if the light sensor detects a low light level potentially indicating evening or night, the second property may configure the dispenser station to output audio reminders at a lower volume level).

As will be understood, the properties may be in any suitable format, such as, for example, JSON format, etc.

In one embodiment, the properties may include commands for a dispenser station to transmit a real-time reminder based on a patient or other factors. In one embodiment, the system receives a behavior command related to C. Diff protocol and is configured to pull and/or receive properties related to the C. Diff protocol, which may include commands and/or programming in which one or more dispenser stations are configured to transmit an audible reminder based on isolation status of the patient (e.g., in response to receiving an indication that someone is within a certain distance of the dispenser station based on a proximity sensor or the like).

In one or more embodiments, the system may be configured to send dispenser station behavior commands to dispenser stations (e.g., without pulling/receiving properties related to the same). In these embodiments (and others) the dispenser stations store may store properties and/or commands associated with the dispenser station behavior commands in memory (e.g., local, remote, and/or distributed).

At step 808, the system promulgates dispenser station behavior command properties to at least one dispenser station. In various embodiments, the system promulgates the dispenser station behavior command properties to at least one dispenser station via a mesh network of dispenser stations. In some embodiments, the system promulgates the dispenser station behavior command properties to at least one dispenser station via wireless protocol (e.g., WiFi, ZigBee, Bluetooth, Bluetooth Low Energy, etc.). In particular embodiments, the system promulgates the dispenser station behavior command properties to at least one dispenser station via a wired connection to one or more dispenser stations. In further embodiments, the system promulgates the dispenser station behavior command properties to at least one dispenser station via a secondary system (e.g., via a hospital system operatively connected to a central computing system and/or one or more dispenser stations; by transmitting the behavior command properties to one or more badges, tags, etc., which then transmit the behavior command properties to one or more dispenser stations; etc.).

Figure 9:
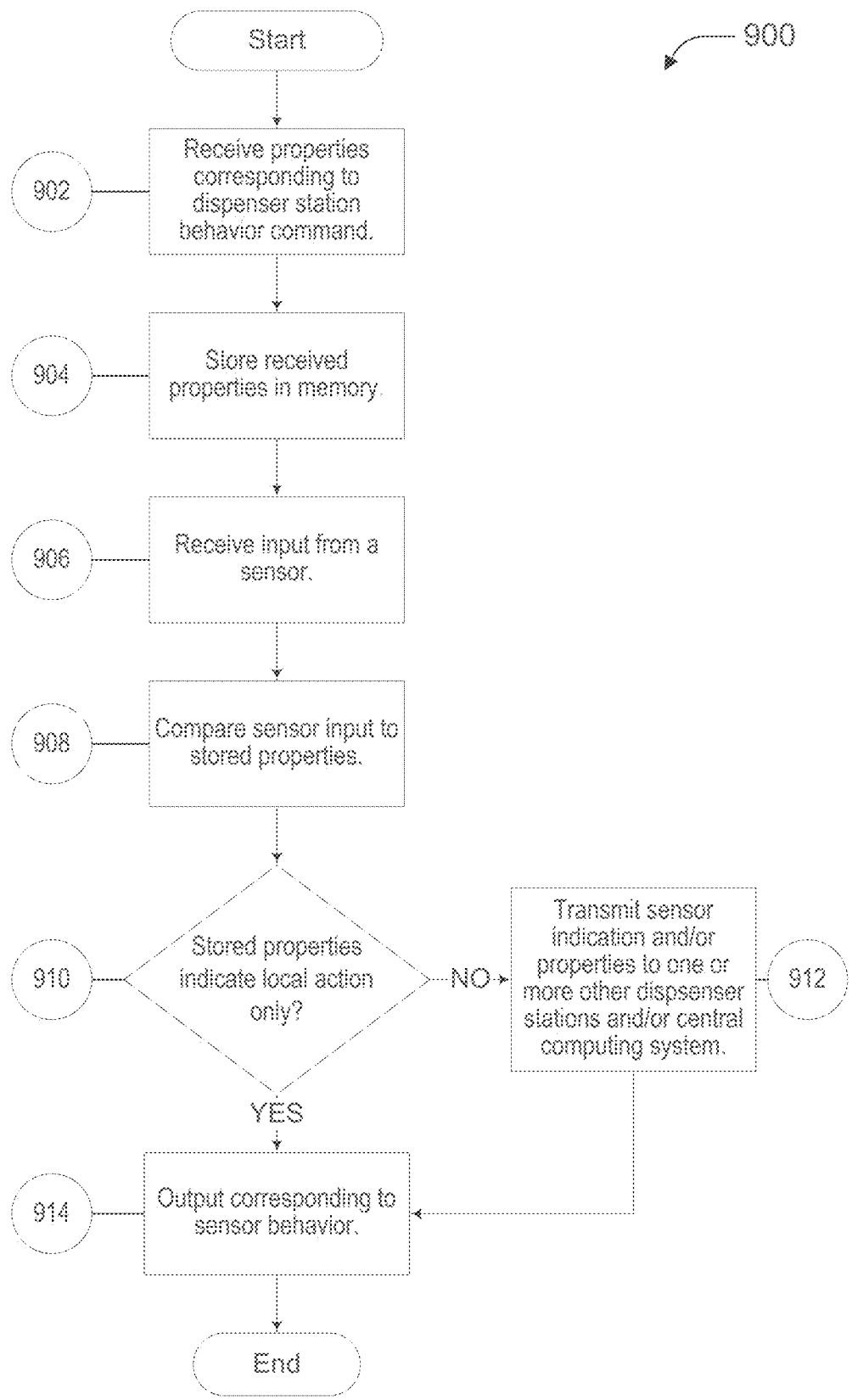
FIG. 9 is an exemplary flowchart illustrating an exemplary behavior command properties implementation process, according to one embodiment of the present disclosure.

FIG. 9 is a flowchart illustrating an exemplary dispenser station. The process begins at step 902, where the dispenser station receives properties corresponding to a received behavior command (e.g., a behavior command as discussed in relation to FIG. 8). In at least one embodiment, the dispenser station receives the behavior command properties from a central computing system (e.g., via a network connection). In at least one embodiment, the dispenser station receives the behavior command properties from another dispenser station (e.g., via a mesh or other network). In some embodiments, the dispenser station retrieves/pulls the behavior command properties from memory and/or the behavior command is loaded on the dispenser station via USB, hardwire, or other medium.

As discussed herein, the dispenser station may receive behavior command properties that change a particular functionality of the dispenser station. In one embodiment, the behavior command properties may change an action executed by the dispenser station in response to a particular sensor input. Continuing with this embodiment, the behavior command properties may correspond to a night shift command/protocol and, based on receiving an indication from a light sensor (e.g., operatively connected to the dispenser station or from another dispenser station), the dispenser station is configured to provide hand sanitization reminders, but at a lower volume (e.g., so as to not disturb sleeping patients).

At step 904, the system stores the received properties in memory. In one embodiment, the architecture of the dispenser station as described in FIG. 2 includes a memory component that stores various data collected, which, in at least one embodiment, may include received properties, sensor data, data received from other dispenser stations, etc. In some embodiments, the system may store the received properties in remote memory (e.g., via a network) and/or distributed databases (e.g., via a blockchain, cloud-based, or other distributed system).

At step 906, the dispenser station receives input from a sensor. As discussed above, the properties corresponding to dispenser station behavior commands may modify the functionality of a dispenser station based on the input received from one or more sensors operatively connected to the dispenser station (see, e.g., FIG. 2). As discussed herein, the dispenser station may receive any suitable input from any suitable sensor, such as, for example, input from a light sensor (e.g., indicating a certain amount of ambient light in a room/area), input from a proximity sensor (e.g., indicating that a person or object is within a certain predetermined distance of the dispenser station), input indicating a particular person, object, or the like is within a certain range of the dispenser station (e.g., the system may be configured to receive a particular identifier or identifiers associated with a particular, person, provider, object, group of providers, group of people, group of objects), etc. As will be understood from discussions herein, the dispenser station may receive the input from the sensor in any suitable way (e.g., via a wired connection, via a wireless connection, via a network connection, via a mesh network, etc.).

At step 908, the system compares received sensor input to the properties stored in memory. As will be understood, the properties stored in memory may be received from a central computing system (e.g., at step 902) or otherwise stored in memory operatively connected to one or more dispenser stations. As discussed herein, the system is configured to compare the received sensor input to the properties stored in memory to determine a next step (e.g., a particular output, a transmission of data to other dispenser stations, etc.).

In one or more embodiments, the system is configured to compare received sensor input to the properties by comparing a numerical value of a sensor input (as received, normalized, and/or converted) to an associated numerical value of one or more properties (e.g., if a received sensor input is a serial number associated with a particular individual (e.g. 1234), the system compares the serial number (1234) to the value of one or more properties (e.g., 2345, 4321, 5432, etc.) to find a match). In some embodiments, the system is configured to compare received sensor input to one or more properties, where the one or more properties include a range to determine whether the received sensor input is within the predetermined range.

At step 910, the system determines whether the stored properties indicate only a local action. As will be understood from discussions herein, a dispenser station may be programmed to take a local action based at least in part on comparing a sensor input (or sensor inputs) to one or more properties. A local action may be, for example, providing an audio and/or visual reminder to an individual to wash their hands and/or use a sanitization device, lowering a volume of all audio reminders for a specific amount of time or until the system receives an additional specific sensor input, or any other suitable action or output by the dispenser station. As will also be understood from discussions herein, depending on the sensor input and the one or more properties, the system may be configured to take action involving additional dispenser stations (in some embodiments, in addition to taking local action).

At step 912, if the system determines that the stored properties do not indicate only a local action, then the system is configured to transmit a sensor indication and/or properties corresponding to one or more other dispenser stations and/or a central computing system. In various embodiments, the system may be configured to take actions involving one or more dispenser stations, including groups and subgroups of dispenser stations based at least in part on input received at one or more sensors at one or more dispenser stations. In these embodiments (and others), the system is configured to transmit information (e.g., sensor data) and/or properties (e.g., instructions) from one dispenser station to one or more additional dispenser stations and/or a central computing system over a network.

As a particular example, the system may identify an individual at a first dispenser station (e.g., via a received identifier or the like), transmit an indication (e.g., one or more properties/instructions) to one or more additional dispenser stations to provide a specific type of reminder to the individual if the one or more additional dispenser stations detect the individual within proximity of the one or more additional dispenser stations.

As discussed above, a dispenser station or group of dispenser stations may be configured to transmit sensor data to a central computing system (to which they are communicably connected) and the central computing system may, in response to receiving the sensor data, transmit properties or other types of commands to various dispenser stations. For example, the system may identify an individual at a first dispenser station (e.g., via a received identifier or the like), transmit an indication to a central computing system, where the central computing system may promulgate properties to one or more additional dispenser stations based on the received indication (e.g., to provide a specific type of reminder to the individual if the one or more additional dispenser stations detect the individual within proximity of the one or more additional dispenser stations).

Dispenser stations may be configured to behave based on information (e.g., sensor input) received at one or more other dispenser stations. For example, one or more dispenser stations may be configured to recognize patterns that may not be identifiable from one individual dispenser station and/or sensor, as such, for example, a group of dispenser stations may share information to distinguish automatically when an individual enters/exits a room within proximity of a dispenser station verses when a stationary object is detected in front of a dispenser station/sensor (e.g., two dispenser stations may identify movement of an individual within proximity of the two dispenser stations). In various embodiments, one or more dispenser stations may also identify when an obstruction or partial obstruction occurs at one dispenser station/sensor and automatically adjust a local dispenser station behavior based on the obstruction (e.g., via one or more properties promulgated by a dispenser station, one or more dispenser stations, via a central computing system, etc.).

In at least one embodiment, the system is configured to control a reminder based on timing or other factors, such as, based on the frequency of patterns of individuals entering or exiting a room. For example, if there is a very high frequency of individuals entering/exiting a patient's room, the dispenser station may control the volume of a reminder, determine whether the a voice reminder was recently played (e.g., and not play a reminder for each person, but for the group as a whole), and/or silence the reminder.

If the system determines that the stored properties indicate only a local action or following the system transmitting a sensor indication and/or properties to one or more other dispenser stations and/or the central computing system (e.g., at step 912), then the system, at step 914, produces an output corresponding to the sensor behavior. As discussed above, the dispenser station may produce any suitable output based at least in part on sensor input. Exemplary outputs may include a reminder to an individual to use hand sanitizer via a speaker or light, changing the volume of the voice reminder based on background ambient noise of the room or hospital unit, changing a visual indicator based on the ambient light level in a patient's room and adjusting the volume of product dispensed or adjusting the type of product that is dispensed based on the role of the individual or the patient in the room, a reminder indicating or recommending soap usage versus hand sanitizer usage if a patient has C. Diff, etc.

In various embodiments, the system uses data analytics to monitor, evaluate, and influence hand hygiene behavior. An exemplary process for using data analytics to monitor, evaluate, and influence hand hygiene behavior is depicted in FIG. 10 and discussed below.

Figure 10:
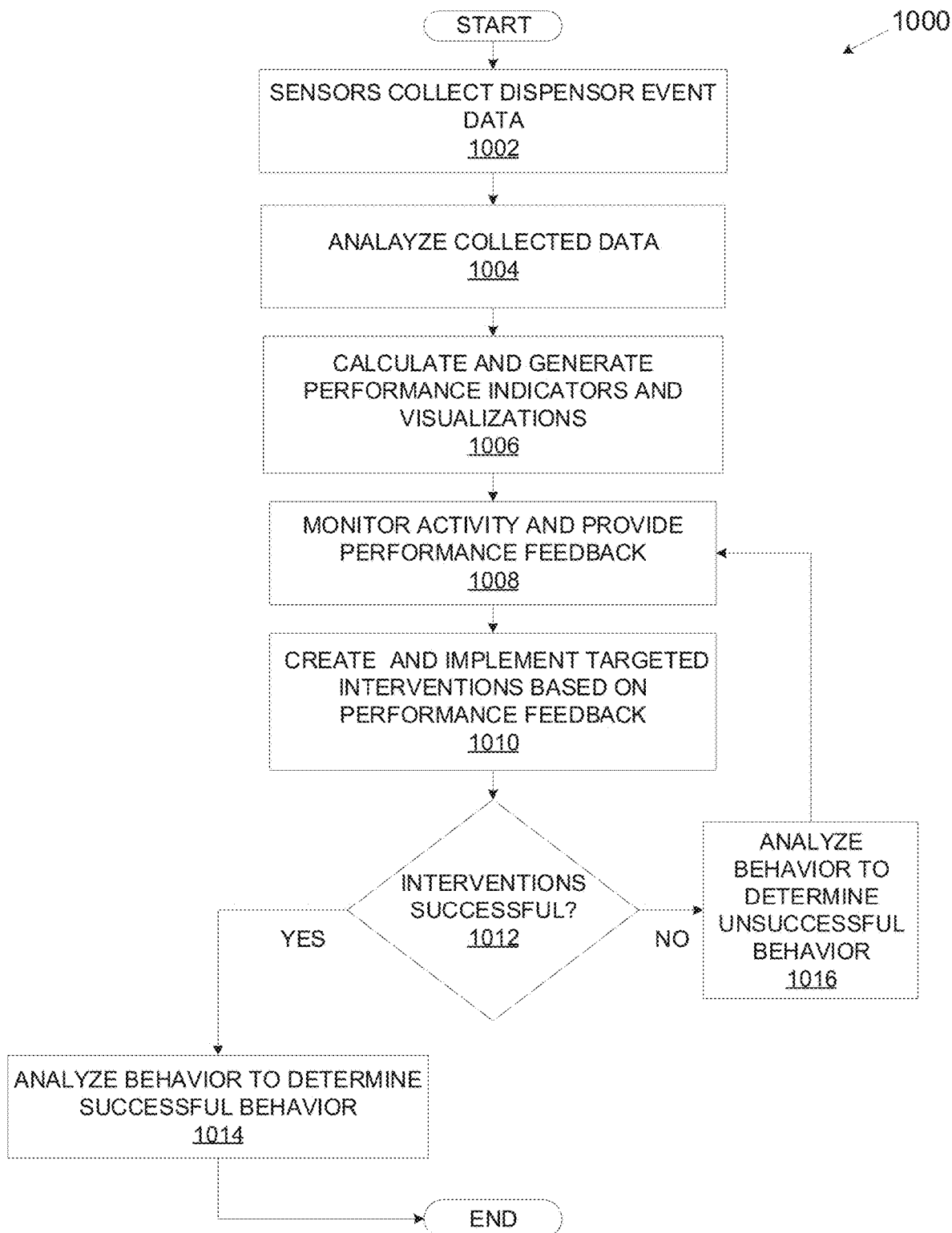
FIG. 10 is an exemplary flowchart illustrating an exemplary data collection, evaluation, and intervention process, according to one embodiment of the present disclosure.

At step 1002 of FIG. 10, sensors collect and/or aggregate data from one or more dispensers operatively connected to a network (e.g., as depicted in FIG. 6). In various embodiments, a step in driving sustained hand hygiene change can be establishing and analyzing collected and/or aggregated dispenser data to establish a baseline and/or history of activity on the dispenser network and all elements contained therein.

Further, various embodiments of the systems and methods presented can be used to help inform various interventions that may drive a process informing and/or dictating hand hygiene practices. For example, the various embodiments of the systems and methods presented may use data collected from a series of hand hygiene monitoring sensors to serve as the foundation for compliance calculations and behavior change. In such an example, data collected from the sensors may be used to determine the time between when a person (e.g., a provider) enters a patient's room and when that person performs a hand hygiene activity.

In various embodiments, the data collected, for instance, in step 1002 of FIG. 10 may include, but are not limited to: 1) which dispensers were used (soap, hallway sanitizer, and in-room sanitizer); 2) when dispensers were used; 3) who used and/or did not use dispensers; 3) how often a dispenser was used; 4) how often a subject or group of subjects used one or more dispensers; and 5) alarm activity and its relationship to dispenser activity.

At step 1004, the system analyzes the collected data. The data may be analyzed via a plurality of methods including, but not limited to: 1) frequency calculations; 2) probabilistic modeling techniques such as multiple linear regression; 3) curve fitting; 4) erroneous and/or outlier data detection and correction; 5) descriptive statistics; and 6) inferential statistics. In various embodiments, the analyses may be completed automatically. In at least one embodiment, data from additional sources, such as time scheduling applications, may be requested by the system, imported into the system, and incorporated into various analyses, calculations, and/or scores.

In various embodiments, the analysis in step 1004 may use a probabilistic modeling technique (e.g., multiple linear regression) to assess the relationship between a variable and one or more of: 1) an individual provider; 2) a provider group; and 3) all providers in a provider organization. In an exemplary instance, a multiple linear regression could be conducted on all providers in a provider organization to identify potential relationships between adjustable system properties (e.g., alert tone volume, frequency, and duration) and hygiene performance. An analysis in the exemplary scenario could better inform the system by identifying aspects of the system (and/or process) with higher statistically demonstrated influence, as compared to other aspects of the system or otherwise, on hygiene performance.

In various embodiments, the system may use erroneous and/or outlier data detection and correction methods to highlight and/or eliminate issues in one or more data sets. In an exemplary instance, an analytical process of step 1004 could establish a baseline level of hygiene activity for a provider group and identify a set of dispensers most frequently used by the provider group. The exemplary analytical process could then highlight (e.g., in step 1006) a recurring instance wherein one dispenser was utilized at a higher level (e.g., four times as often) than established baseline data would predict while one or more other dispensers were utilized at a much lower level than established baseline data would predict (e.g., half as often). In this instance, the highlighting of outlier data could allow a user to infer that the one or more dispensers reporting lower utilization may be empty, improperly located, malfunctioning, etc. In various embodiments, such analyses could utilize additional data to permit inferences and results with even greater specificity.

At step 1006, the system calculates and generates one or more performance indicators and visualizations based, for example, on data collected in step 1002 and analyzed in step 1004. In various embodiments, the one or more performance indicators and/or visualizations could be, but are not limited to; 1) compliance, where compliance may be expressed as a numeric ratio computed by comparing expected hygiene activity with actual hygiene activity; 2) proactivity, wherein proactivity may be expressed by a numeric value computed by comparing one or more dispenser events wherein hand hygiene product was dispensed to the subset of the one or more dispenser events where no notifications (e.g., tones, verbal reminders, etc.) were issued by a dispenser before a hand hygiene product was dispensed (or other activity occurred); and 3) histograms where the frequency of one or more dispenser events of a selected criteria may be displayed visually.

In various embodiments, compliance, as a performance indicator, may be calculated at an individual provider, provider group, or provider organization level. Compliance may be the ratio of expected hygiene activity, which may be automatically established, to actual hygiene activity, as indicated by data collected in dispenser events. An exemplary compliance ratio may be computed via dividing a sum of dispenser events (e.g., a dispenser detector is activated) for a subject (e.g., individual provider, group, etc.) and in a selected period of time (e.g., 3 days) by the sum of those dispenser events wherein hand hygiene product was dispensed to the subject. In this instance of a compliance ratio calculation, the ideal ratio may be 1. In various embodiments, the ratio may reflect the quality of performance of one or more subjects in adhering to one or more policies established by an individual provider, provider group, and/or provider organization.

In at least one embodiment of the system and methods presented, a compliance ratio may be calculated by automatically establishing the number of times a provider should have used one or more dispensers (e.g., based on proximity data, etc.) in a set of instances, then comparing that number to the actual number of times the provider used the one or more dispensers in the set of instances.

In various embodiments, proactivity, as a performance indicator, may be calculated at an individual provider, provider group or provider organization level. Proactivity may be the percentage of the subject dispenser events in the selected period of time wherein the subject acquired hand hygiene product from the dispenser and the corresponding dispenser did not issue a notification (e.g., a tone, verbal reminder, etc.) beforehand for the purpose of reminding the subject to dispense hand hygiene product. An exemplary proactivity percentage may be computed via dividing the sum of dispenser events in a selected period of time by the sum of the subset of the dispenser events wherein hand hygiene product was dispensed and a reminder notification was not issued, then multiplying the quotient by 100. In an exemplary instance of a proactivity percentage calculation, the ideal percentage may be 100%. In various embodiments, the percentage may reflect the quality of performance of one or more subjects in autonomously adhering to one or more hygiene policies established by an individual provider, provider group, and/or provider organization.

In various embodiments, the system may use the above metrics and others to provide insight into hand hygiene activities and/or dispenser configurations and, as a result, obtain information regarding the performance of subjects in the system as well as the performance of the dispensers that form a portion of the system. In at least one embodiment, the system may use metrics to determine a time that is required for a provider to reach one or more hand hygiene product dispensers (e.g., 2-60 seconds) before a notification is issued. In an exemplary instance, if the majority of a provider group collectively demonstrates a consistently low calculated hygiene proactivity (e.g., less than 25% for at least three days), a system administrator may infer that the hand hygiene product dispensers in the vicinity of the group may require adjustment of settings such that there is a greater delay between the identification of a provider in proximity to a dispenser and the use of a notification by the dispenser.

In various embodiments, the system may represent hand hygiene activity data on visualizations, graphical and otherwise, such as histograms to indicate performance. In at least one embodiment, the system may generate a histogram by: 1) computing one or more sums of instance of one or more events, in a select period of time, with and/or without selected criteria and, wherein, the sums may be computed on a selected basis (e.g., individual provider, weekly, above a threshold, etc.) and may represent the frequency of occurrence for an event with and/or without selected criteria and in the select period of time; 2) generating a histogram using a computational system function and based on the frequencies, wherein the selected basis is used to generate respective sections of the histogram; and 3) creating labels for various components of the histogram (e.g., titles, axes, etc.). In various aspects, a histogram may visualize and express the frequency of events with and/or without select criteria. Exemplary frequencies that may be visualized in a histogram include, but are not limited to; 1) the frequency of dispenser events, wherein hand hygiene agent was dispensed, in a given time period (e.g., 3 days), and the basis is individual providers in a provider group; and 2) the frequency of dispenser events, wherein notifications were issued before hand hygiene agent (e.g., product, such as soap or hand sanitizer) was dispensed, in the given time period, and the basis is provider groups in an provider organization.

In various embodiments, the system may present one or more histograms in which a frequency distribution is computed and/or presented discreetly, as in the above instances, or relatively. In an exemplary embodiment, a histogram may compute and present a relative frequency of dispenser events on a provider group basis, wherein hand hygiene agent was dispensed without a notification issued beforehand. In this instance, the relative frequency may be computed by dividing the respective criteria-matching event sum for each provider group by the total number of individual providers in the corresponding group, and the resulting histogram constructed via the methods described herein will illustrate the frequency of dispenser events across one or more provider groups in a manner which is independent of provider group population and, thus, may permit a greater degree of accurate and/or easy comparison of provider group performance.

In at least one embodiment, one or more histograms may depict the time between when respective individual providers perform hand hygiene relative to when they enter or exit a patient's room. The one or more histograms may represent data from one or more rooms and may be aggregated to have a more comprehensive understanding of hand hygiene performance. In this instance, the system may analyze or inspect the one or more histograms to identify key aspects indicating the performance of present system configuration timings and/or providers. For example, inspection of the one or more histograms which demonstrates a varied distribution amongst individual providers may indicate poor performance amongst those individual providers with lower frequencies of the select criteria.

At step 1008, the system monitors activity and provides performance feedback. In at least one embodiment, such performance feedback includes, but is not limited to, analyses, scores, and other meaningful insights generated in steps 1004 and 1006. As will be understood from discussions herein, performance feedback may be used for real-time feedback and reporting to improve the hand hygiene compliance performance of specific groups of providers and/or individual providers. In at least one embodiment, feedback may lead to the use of one or more interventions (as described in relation to step 1010, below) to potentially assist in various objectives including, but not limited, hand hygiene improvement, sustained hand hygiene performance, and furtherance of other organization protocols and/or measures.

In various embodiments, the system may deliver and/or design feedback and other data and/or data insights to be easily interpreted and managed by one or more persons including, but not limited to: 1) hospital leadership; 2) provider group supervisors; 3) system administrators; and 4) individual providers. Exemplary delivery mechanisms of the above description may include, but are not limited to; 1) push notifications on hygiene activity and/or events to electronic devices on the provider organization network or otherwise; 2) individual and/or group—specific email and/or short messaging service (SMS) text alerts on hygiene activity and/or events; and 3) hygiene activity visualizations pushed to electronic devices, such as screens, connected to the system. Various embodiments of the above may include, but are not limited to: 1) text-based summary reports consisting of individual provider, provider group, and/or provider organization descriptive statistics (e.g., mean, median, range, etc.); 2) graphical visualizations of the same; and 3) automatically drafted insight reports highlighting dispenser states, hygiene events, statistically influential variables (as determined in a probabilistic model of step 1004), and/or targeted interventions (created and implemented for example as described at step 1010).

In one or more embodiments, the system may further implement the above exemplary delivery mechanisms and other mechanisms, and deliver one or more notifications based on workflow data. In various embodiments, the one or more notifications may be specific to an individual provider, a provider group, and/or other subsets of providers. In at least one embodiment, the one or more notifications may include workflow data pertaining to and be delivered to a subset of providers presenting unusually high patient interactions. In some embodiments, the one or more notifications may include workflow data pertaining to and be delivered to a subset of providers presenting unusually low patient interactions. In various embodiments, one or more subsets of providers may include, but are not limited to: 1) one or more providers observed (e.g., by the system) to operate in a specific region of a hospital; 2) one or more providers observed (e.g., by the system) to operate within a given window of time, such as a current window of time; and 3) one or more providers observed (e.g., by the system) to operate in correlation with one or more patterns of behaviors and/or with respect to one or more other factors.

In various embodiments, one or more providers may be assigned (e.g., via the present system or another system of an organization) to one or more specific groups, one or more specific floors, and/or other designations. In one or more embodiments, the present system may collectively refer to information regarding assignment to the one or more specific groups, one or more specific floors, and/or other designations as "assignment data." In at least one embodiment, the present system may receive (e.g., as an input to the system) assignment data regarding group, floor, and/or other designations of the one or more providers.

In one or more embodiments, the system may use one or more system aspects, features, and/or inputs to identify the one or more subsets of providers described herein and other subsets of providers. In various embodiments, the system may incorporate system aspects, features, and/or inputs including, but not limited to: 1) hand hygiene data (e.g., as collected by the system); 2) floor assignments pertaining to one or more providers; and 3) location data (e.g., as inferred by activity data collected by the system) in relation to one or more location parameters (e.g., geofences).

In at least one embodiment, the system may identify the subset of providers with unusually high or low patient interaction by conducting operations including, but not limited to: 1) indexing patient interaction data (e.g., as indicated by hand hygiene data) pertaining to a greater subset of providers, wherein the greater subset of providers contains the subsets of providers with unusually high or low patient interaction; 2) computing the geometric mean of patient interactions for the greater subset of providers over a given time period (e.g., one week); 3) computing the standard deviation of the patient interactions for the greater subset of providers over the same given time period; and 4) indexing one or more providers (e.g., the subset of providers) in the greater subset of providers, wherein the respective and corresponding patient interaction for the one or more providers (e.g., the unusually high interaction subset) reaches two standard deviations or more above the mean, or (e.g., the unusually low interaction subset) falls two standard deviations or more below the mean.

In various embodiments, the system may count a respective number of times one or more providers enter a location, such as a patient's room, and/or dispenses antiseptic solution (e.g., via a dispenser as described herein) at the location. In one or more embodiments, if the respective number of times counted by the system exceeds a threshold, the system may take one or more actions such as alerting (e.g., via transmitted electronic notification) a provider and/or an immediate supervisor to the provider.

In at least one embodiment, because the system may read a provider's badge, the system may know if one or more providers are currently working. In some embodiments, the system may receive a schedule or clock in or log in associated with a particular provide indicating that the particular provider is currently working or currently working in a particular setting (e.g., on a particular floor, part of a particular unit, etc.). In various embodiments, the system may deliver notifications and/or alerts, such as when necessitated by an emergency situation, to all of the one or more providers currently working.

At step 1010, the system may create and implement targeted interventions based on performance feedback. Exemplary interventions that may be created and implemented to address one or more hand hygiene matters (as discussed above) include, but are not limited to: 1) communications, such as notifications and/or warnings, delivered via audio, electronically, and/or via text to one or more subjects supervising, contributing to, or otherwise embodying the hand hygiene matter, and wherein the communication summarizes the one or more hand hygiene matters and dictates appropriate responses such as increasing the frequency of dispenser use (e.g., increasing compliance), decreasing the instance of dispenser notifications issued before dispenser use (e.g., increasing proactivity), and others; 2) intervention meetings, wherein the one or more subjects convene, in person or otherwise, to discuss appropriate responses such as those described above; and 3) implementation of pre-programmed and/or customized audio messages and/or warnings to be issued by one or more dispensers to the one or more subjects upon triggering of a sensor and recognition of the one or more subjects by the one or more dispensers.

Various embodiments may implement interventions based less in corrective measures (e.g., as is generally the case in the interventions described above), but more in the promotion and continuation of specific hand hygiene practices. Such interventions may include, but are not limited to; competitions among within and between individual providers, provider groups (e.g., nurses vs doctors), teams of providers (e.g., randomizing providers to different competition teams), and an entire provider organization. In an exemplary intervention implementing a competition between randomized teams of providers, various embodiments of the system may, upon command, randomly generate lists of team members (e.g., individual providers) based on specified criteria, such as number of lists and respective list length, and output those lists to a system administrator or other intervention supervising and/or coordinating user. In the instance of a competition-based intervention, randomly generated teams may be monitored over a specific period of time (e.g., one week), where the performance of the team, as a combination or otherwise of the respective individuals, is tracked. Methods of performance tracking may include, but are not limited to, observation of changes or lack thereof in performance indicators (e.g., compliance and/or proactivity) and/or visualizations (e.g., histograms) over the specific period of time, wherein rewards such as cash prizes, recognition, etc. may be granted to teams and/or their respective members which demonstrate a shift or lack thereof in performance indicators and or visualizations over and/or after the specific period of time.

At step 1012 the system determines whether an intervention was successful. In various embodiments, the system may evaluate one or more effects of implemented interventions. In some embodiments, intervention success may be evaluated by a variety of evaluation methods and may be conducted automatically. Evaluative methods may include, but are not limited to: 1) analyzing, in isolation and/or as a combination, the descriptive statistics (e.g., mean, median, etc.) of individual providers, provider groups and/or provider organizations; 2) calculating and interpreting performance indicators such as compliance and proactivity, as discussed herein; and 3) inspecting histograms and/or other data visualizations, as discussed herein or otherwise.

In at least one embodiment, a successful intervention may be defined as a shift in the value or quality of one or more performance indicators, including those described herein and otherwise, towards one or more automatically established performance benchmarks, wherein the performance benchmarks and corresponding performance are established by the generation and/or computation of various evaluative and analytical performance indicators. Indicators of success may include, but are not limited to: 1) shifts towards an established benchmark in one or more computed compliance ratios (e.g., shifts towards a ratio of 1); 2) shifts towards an established benchmark in one or more computed proactivity percentages (e.g., shifts towards a percentage of 100%); 3) shifts towards an established benchmark in the distributions, respective and otherwise, of histograms; and 4) other shifts of a performance indicator towards an established benchmark. The analysis of these patterns may be designed to provide insights into, for example, directing the scope, hygienic or otherwise, of individual and/or group providers and any associated interventions.

In particular embodiments, the system may identify, potentially after a group intervention, which individual providers may require more focused hand hygiene improvement efforts. An example process for identifying and improving hand hygiene may use the distribution of providers based on a combination of individual hand hygiene performance and/or the number of times that a particular provider should perform hand hygiene. Methods, such as those described herein, may then be used to target a manageable subset of providers that may be classified as under-performers. In various embodiments the identification of specific providers, based on specific criteria, may be conducted automatically via the methods described herein.

At step 1014, the system, upon determining that one or more interventions was successful (as discussed above, in relation to step 1012), determines one or more behaviors which led to a successful behavior change (or intervention). The one or more behaviors of those described above may be characterized by the combination of and/or individual use of various methods including, but not limited to, the computation and/or generation of one or more iterations of one or more performance indicators and/or visualizations (e.g., histograms) over a selected time period (e.g., 2 weeks) and within specific time intervals (e.g., once per day) occurring immediately after the implementation of an intervention, depicted in step 1010, and an additional time period equal to a proportion (e.g., 25%) of the selected time period, wherein the additional time period is a selection of time occurring immediately prior to the implementation of the intervention.

In various embodiments, the one or more performance indicators and/or visualizations may be further inspected automatically (e.g., by the system) to detect one or more changes and/or trends in the results and/or underlying variables contributing to those results (e.g., dispenser events wherein hand hygiene product was dispensed and/or a notification issuance was not required) over the specific time intervals of the selected time periods which may have contributed to a desired shift (e.g., towards benchmarks) in the one or more performance indicators and/or visualizations. In various embodiments, additional data such as room assignments and/or other workflow data may also be analyzed and aggregated with the one or more performance indicators and/or visualizations to further identify factors which may contribute to successful behaviors. In one or more instances, a detected change that may indicate a behavior contributing to successful behavior could include: 1) a consistent (e.g., per event) decrease in the frequency of notification issuances prior to hand hygiene product dispensing (e.g., consistent increases in proactivity) following the intervention; 2) a consistent increase in dispenser events wherein hand hygiene product was dispensed (e.g., consistent increases in compliance) and, wherein, there was not an observed decrease in average dispenser events (e.g., as calculated by computing the mean daily dispenser events over the additional time period occurring immediately prior to the intervention); and 3) other changes, consistent and otherwise, which are found to contribute to the shift in the one or more performance indicators and/or visualizations.

At step 1016, the system, upon determining that one or more interventions was unsuccessful (or failed, as discussed above, in relation to step 1012), determines one or more behaviors which led to the unsuccessful intervention, wherein the unsuccessful intervention may be defined as a lack of shift toward a desired benchmark and/or an undesired shift (e.g., away from established benchmarks) in one or more performance indicators and/or visualizations following an intervention. The one or more behaviors of those described above may be characterized by the combination of and/or individual use of various methods including, but not limited to, the computation and/or generation of one or more iterations of one or more performance indicators and/or visualizations (e.g., histograms) over a selected time period (e.g., 2 weeks) and within specific time intervals (e.g., once per day) occurring immediately after the implementation of an intervention, depicted in step 1010, and an additional time period equal to a proportion (e.g., 25%) of the selected time period, wherein the additional time period is a selection of time occurring immediately prior to the implementation of the intervention.

In particular embodiments, the one or more performance indicators and/or visualizations may then be further inspected automatically (e.g., by the system) to detect one or more changes and/or trends in the results and/or underlying variables contributing to those results (e.g., dispenser events wherein hand hygiene product was dispensed and/or a notification issuance was not required) over the specific time intervals of the selected time periods which may have contributed to the lack of and/or the undesired shift in the one or more performance indicators and/or visualizations. In various embodiments, additional data such as room assignments and/or other workflow data may also be analyzed and aggregated with the one or more performance indicators and/or visualizations to further identify factors which may contribute to successful behaviors. In one or more embodiments, a detected change that may indicate a behavior contributing to unsuccessful behavior may include: 1) a consistent (e.g., per event) increase in the frequency of notification issuances prior to hand hygiene product dispensing (e.g., consistent decreases in proactivity) following the intervention; 2) a consistent decrease in dispenser events wherein hand hygiene product was dispensed (e.g., consistent decreases in compliance) and, wherein, there may or may not be an observed increase in average dispenser events (e.g., as calculated by computing the mean daily dispenser events over the additional time period occurring immediately prior to the intervention); and 3) other changes, consistent and otherwise, which are found to contribute to the lack of and/or the undesired shift in the one or more performance indicators and/or visualizations.

In various embodiments, the system may be configured to automatically identify, capture, and report (e.g., to hospital leadership and/or others) the identifiers and/or one or more performance indicators and/or visualizations of individual providers and/or providers groups with markedly high and/or low performance, where the thresholds for high and/or low performance may be configured automatically and may be discreet or relative to other performance and/or other data.

In an exemplary system configuration, the histograms of any and/or all the one or more individual providers and/or provider groups, where a set of high performance criteria are met, may be captured and reported in the manner described above and/or other manners. Exemplary high performance criteria may include, but is not limited to; 1) a compliance ratio, computed as described herein and over a specific selection of time (e.g., 1 week), less than or equal to 1.11 (e.g., 90% or greater compliance); and 2) a proactivity percentage, computed as described herein and over the specific selection of time, greater than or equal to 90%. By analyzing, as in step 1014, the histograms and/or other performance indicators and/or visualizations of these top performers, behaviors which may contribute to successful behavior may be identified.

In an exemplary system configuration, the histograms of any and/or all the one or more individual providers and/or provider groups, wherein a set of low performance criteria are met, may be captured and reported in the manner described above and/or other manners. Exemplary low performance criteria may include, but is not limited to; 1) a compliance ratio, computed as described herein and over a specific selection of time (e.g., 1 week), greater than or equal to 1.43 (e.g., 70% or less compliance); and 2) a proactivity percentage, computed as described herein and over the specific selection of time, less than or equal to 50%. By analyzing, as in step 1016, the histograms and/or other performance indicators and/or visualizations of these top performers, behaviors which may contribute to unsuccessful behavior may be identified.

In various embodiments, identified behaviors that may contribute to successful and/unsuccessful behaviors may be included in one or more reports, notifications, and/or other communications produced by the system and delivered to one or more individual providers, provider groups, the provider organization and/or hospital leadership.

In various embodiments, the systems and methods herein identify which providers are achieving a particular successful or unsuccessful performance, but also provide insights into why their behavior may or may not be successful and/or comparable against means and/or expectations. Methods may consider a variety of factors including, but not limited to: 1) combined data based on hospital providers hand hygiene compliance; 2) workflow data; and 3) dispenser data. In an exemplary embodiment, this data may be used to calculate measures and/or parameters such as an adjusted compliance percentage based on a provider's workflow patterns. In various embodiments of the systems and methods presented, an adjustment of the above description may include, but is not limited to, factors such as aggregate data among multiple health systems, individual facility/unit data, data specific to individual provider types, and data from an individual provider data.

In various embodiments wherein an intervention is evaluated to be unsuccessful and, as a result, provider behavior is analyzed to determine contributing and/or causal factors, a return to electronic monitoring and creation of performance feedback (e.g., as depicted in step 1008) may be implemented.

The present systems and methods generally relate to novel algorithms, software, firmware, and hardware that enable real-time analysis and notification methodologies for creating and transmitting alerts regarding potential high risk situations and for determining workflow patterns. In various embodiments, the system includes a network of sensors that includes, but is not limited to: 1) sensors embedded in tags attached to employee credentials; 2) sensors on one or more hand hygiene agent dispensers, and 3) other sensors located throughout a facility. In one or more embodiments, the systems and methods include a combination of sensors, a sensor network, analytics algorithms and servers, and methodologies for notifying and calculating workflow patterns of staff and for identification of high risk situations.

In at least one embodiment, the present systems and methods leverage data collected by a series of sensors that are installed (e.g., in dispensers and provider tags) throughout a hospital and/or patient care rooms. In one or more embodiments, the sensors collect information related to the location of healthcare providers, patients, visitors, or other individuals throughout a facility or room. In various embodiments, the sensors, either in aggregate or individually, detect the presence of individuals and groups of individuals and identify who the individual is, whether the patient in the room, and which room the provider is in. In at least one embodiment, the system makes determinations using an aggregate of sensors and one or more signal parameters that may be aggregated and analyzed by the sensors and/or at a central processing environment (for example, at a central computer, a cloud environment, etc.).

In various embodiments, determination of the specific data may be made by one or more sensors throughout a hospital's facility. In at least one embodiment, determinations may be made dynamically through a combination of calculations from the one or more sensors as well as additional servers or computers. In some embodiments, the system may collect and aggregate data from multiple sensors, that may or may not be in continual communication with one another, to determine locations of individuals, workflows, and/or potentially high-risk situations. In one or more embodiments, the system may rely on calculations from multiple sensors for synchronous and/or asynchronous communication that may be combined to create an aggregated picture of a provider's workflow (e.g., a series of movements/locations for a given task).

In various embodiments, the one or more sensors collect, store, and transmit data to one or more servers or computers for analysis. In at least one embodiment, the system analyzes, captures, aggregates, and processes data from the one or more sensors to identify anomalies or patterns that may indicate (based on the processed data) that there is a high risk or atypical situation based on data collected by the sensor or network of sensors. In one or more embodiments, the data that is used for the analysis may be a combination of isolated individual data elements that are historic or detected in real/near-real time as well as aggregated and/or other historic data.

In some embodiments, the one or more sensors include electronic devices (e.g., tags, as described herein) that are worn on or carried by providers and/or patients. In at least one embodiment, a tag may be attached to a provider's hospital's credentials (but is a distinct part). As described herein, each tag may further include a unique provider serial number or other provider identifier that is associated with a particular provider wearing the tag. Thus, in various embodiments, each tag is uniquely paired with each provider via a provider identifier. In at least one embodiment, the tag includes the provider identifier in any transmission or communication activities, thus associating any transmissions or communications (from the tag) with the particular provider wearing the tag.

In various embodiments, the tag may also receive, aggregate, and transmit data from a plurality of sensors. For example, a tag may receive and aggregate (at a processor therein) data from one or more sensors (e.g., operatively connected to the tag) and may transmit (via an RF chip) the aggregated data to a central computing station, to a data collection server, to one or more dispensers, etc. In one or more embodiments, data aggregation may occur via local wireless communication methods (for example, RF using protocols such as Bluetooth, NFC, etc.) or via traditional networks (e.g., WiFi, cellular, etc.).

In various embodiments, the tags provided herein may include components for radio frequency communication (henceforth referred to as RF transmission or RF). For example, the tag may include at least one RF module configured to transmit and receive communications from one or more sources including, but not limited to: 1) one or more other tags; 2) one or more dispensers; 3) one or more central computing and/or processing stations; 4) one or more sensors; and 5) any source capable of receiving and/or transmitting RF transmissions. Further, as described herein, the tags may both receive and transmit via RF and, in particular, may transmit in both high and lower power modes.

In various embodiments, the tag may contain one or more sensors that can determine when the provider is in motion, the velocity, the speed, and/or acceleration of the provider, the number of steps a provider has taken, the timing associated with motion and/or steps, the time that the tag was in motion, the time between steps/motion and the time the tag was last detected by one or more sensors. In one or more embodiments, the one or more sensors of an exemplary tag may include, but are not limited to: 1) an accelerometer; 2) a gyroscope; 3) one or more tilt sensors; 4) a vibration sensor; 5) a global positioning system ("GPS") sensor; and 6) one or more other sensors. In various embodiments, the tag includes a time keeping module that provides accurate time tracking capabilities to the one or more sensors. In various embodiments, the tag includes at least one tag processor that receives data from the one or more sensors. In one embodiment, the at least one tag processor may be connected to memory and may be configured to compare received sensor data to one more stored and/or computed thresholds.

In at least one embodiment, a tag (and one or more sensors therein) may provide and transmit data, to the system, that can be used to calculate the number of steps, activity, and/or location of the providers (e.g., providers wearing or carrying the electronic tags). In various embodiments, the tag includes a transmission module (which may be the RF module described above) that can communicate or transmit data using one or more power levels based on a desired application. In at least one embodiment, the multi/varied power transmission may be either manually and/or automatically controlled. In one or more embodiments, automatic control of transmission power may be programmatic (e.g., based on one or more parameters of the sensor or of the overall system) and may be dependent upon threshold comparisons performed within the transmission component, and/or communications from the one or more sensors. In one example, a transmission module of a particular tag may periodically transmit a low power signal that would not be detectable over long distances (e.g., through rooms) and a high power signal that would be detected over long distances (e.g., through multiple rooms) by one or more sensors. In at least one embodiment, if a tag is determined to be in motion (e.g., by a transmission component therein), a transmission component therein may switch into a high power broadcast mode, then return to a low power broadcast mode when the tag is determined to have returned to an idle state.

In one or more embodiments, the transmission module may leverage any suitable electronic communication mode that is sufficient for transmitting and receiving communications between the tag and a central computing station, a data collection server, one or more dispensers and one or more other tags. In at least one embodiment, electronic communication modes leveraged by the transmission module may include, but are not limited to: 1) radio frequency (RF); 2) cellular; 3) Bluetooth; 4) Zigbee; 5) WiFi; 6) near field communication (NFC); 7) ultra wideband; and 8) other communication modes.

Figure 11:
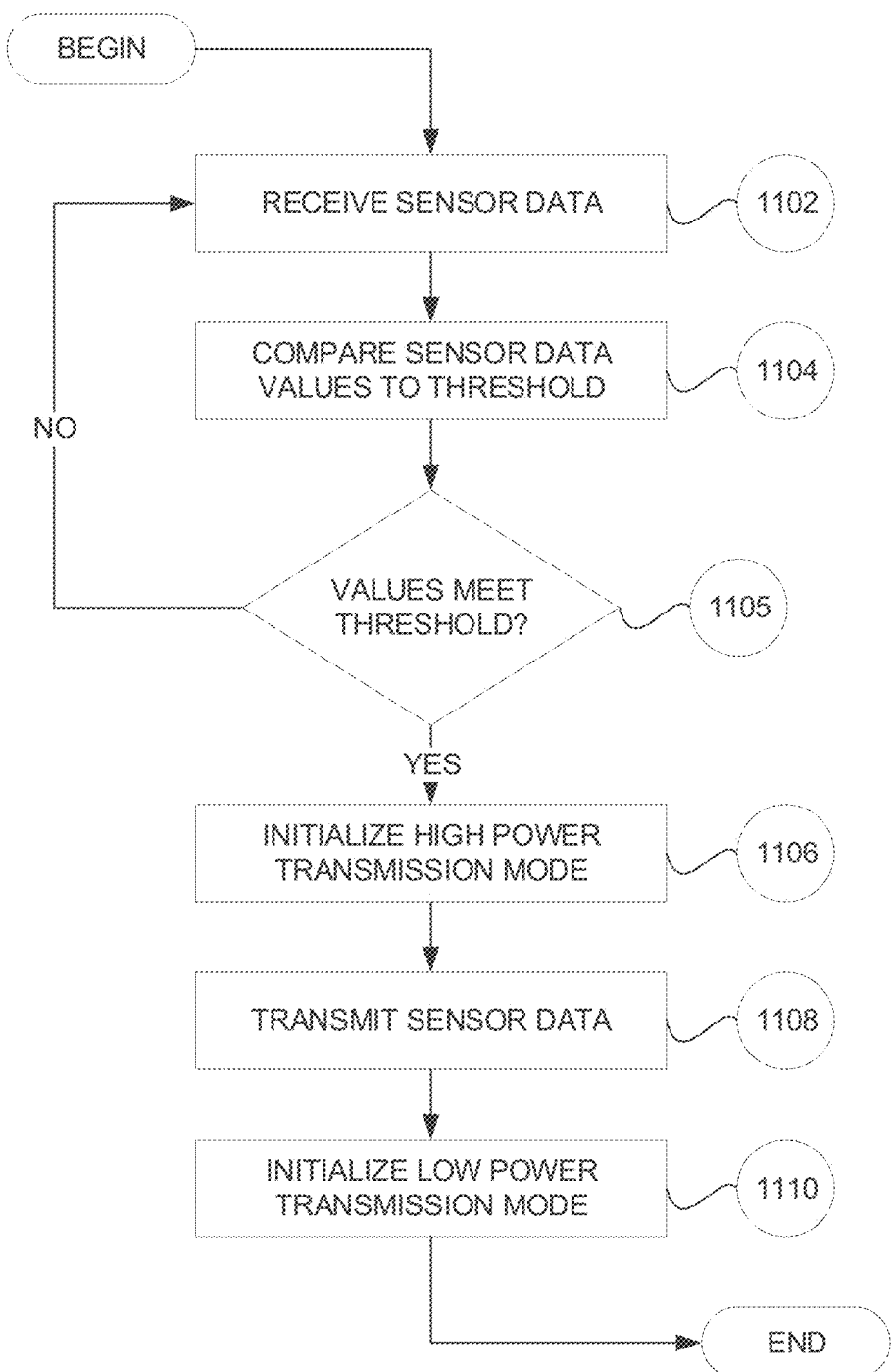
FIG. 11 is a flowchart illustrating an exemplary data collection, evaluation, and transmission process, according to one embodiment of the present disclosure.

FIG. 11 is a flowchart illustrating an exemplary data collection, evaluation and transmission process, according to one embodiment of the present disclosure. In particular, the flowchart of FIG. 11 describes a process by which a tag (as described herein) may adapt transmission parameters based on received sensor data.

At step 1102, a tag (e.g., worn by a provider, attached to hospital equipment, attached to a hospital bed, etc.) receives, at a tag processor therein, sensor data from one or more sensors contained therein or otherwise in communication with the tag. In various embodiments, the sensors may include, but are not limited to: 1) one or more accelerometers; 2) one or more gyroscopes; 3) one or more tilt sensors; 4) one or more vibration sensors; and 5) one or more other sensors. In at least one embodiment, the tag processor may process and/or analyze the sensor data may to extract and/or compute one or more metrics. For example, the tag processor may receive sensor data from an accelerometer (e.g., that is also disposed within the tag) and process the sensor data to compute a step frequency count. In one or more embodiments, the tag processor may automatically and/or continuously receive sensor data from any and/or all sensors disposed within the tag or in communication with the tag (e.g., via the transmission module).

At step 1104, the tag processor may compare the received sensor data (or a processed and/or analyzed derivative thereof) to one or more thresholds and determine if the one or more thresholds are met and/or exceeded. Thus, in various embodiments, the tag may store (e.g., in a memory module thereof) the one or more thresholds. In at least one embodiment, the tag stores, in memory, at least one threshold for each sensor contained therein. In some embodiments, the one or more thresholds may be a combination of pre-defined thresholds (for example, a maximum acceleration, maximum tilt, etc.) and dynamically calculated thresholds (for example, consistently increasing acceleration, tilt, etc.). At step 1105, in one or more embodiments, if the tag processor determines that the sensor data (or derivative thereof) does not meet and/or exceed the one or more thresholds, the tag processor returns to step 1102 and receives additional data (e.g., and proceeds to step 1104, thus repeating the process). In various embodiments, if the sensor data (or derivative thereof) is determined to meet and/or exceed the one or more thresholds, the tag proceeds to transmission activities.

At step 1106, upon determining that the received sensor data (or derivative thereof) meets and/or exceeds the one or more thresholds, the tag processor initializes a transmission module (as described herein) to operate in a high power transmission mode. In at least one embodiment, the transmission module may include one or more discrete components for operating in a high power transmission mode. Thus, in one embodiment, initialization of high power transmission mode may include providing power to the one or more discrete components. In various embodiments, while in the high power transmission mode, the transmission module may transmit at a strength sufficient to pass through one or more interior walls of a facility and sufficient to communicate with one or more components present in a facility. In one or more embodiments, the transmission module may remain in the high power transmission mode until sensor data (or derivative thereof) has been successfully transmitted to the one or more components present in the facility. In at least one embodiment, the tag may configure the transmission module for momentary or protracted high power transmission in response to a received command (for example, a command received from the system as part of a pre-programmed response to an identified pattern).

At step 1108, the transmission module, configured for high power transmission, transmits the sensor data and associated information to one or more components present in a facility. In at least one embodiment, the transmission module may leverage a communication protocol including but not limited to: 1) Zigbee; 2) Bluetooth; 3) WiFi; and 4) other radio communication protocols. In various embodiments, a transmission of a transmission module includes, but is not limited to: 1) sensor data; 2) time data associated with or included in the sensor data; 3) a provider identifier (as described herein); and 4) other tag and/or provider information. Thus, the tag may communicate, via high power transmission, any sensor data that meets and/or exceeds one or more thresholds.

At step 1110, the tag processor may initialize the transmission module to operate in a low power transmission mode. In one or more embodiments, following reconfiguration, the tag continues to receive sensor data and perform threshold comparisons (e.g., repeating the steps described herein and illustrated in FIG. 11). In various embodiments, while in the low power transmission mode, the tag may continue to transmit the provider identifier to one or more nearby dispensers (especially in response to receipt of an RF interrogation signal from the same).

In at least one embodiment, the tag processor may send a "dormant" command to the transmission module and initialize the transmission module to operate in a dormant state. Thus, in one or more embodiments, upon receipt of the "dormant" command, the transmission module may cease communicating in a high power and/or lower power transmission mode, and operate in a passive mode until receipt of a command (from the tag processor) that "wakes" the transmission module from the dormant state. For example, in one embodiment, if a tag processor determines (based upon data received from one or more sensors) that a provider (wearing a tag containing the tag processor) has not taken a step and/or changed locations for a pre-determined time interval, the tag processor sends a "dormant" command to a tag transmission module, causing the module to enter a dormant state.

In various embodiments, the system may receive and transmit communications to and from one or more electronic devices (for example, electronic devices carried by a provider). In one or more embodiments, the system may receive sensor data from the one or more electronic devices. For example, the system may receive sensor from a fitness tracker and/or from a smartphone. In at least one embodiment, the system may include executable program code that (when installed in an electronic device) enables and facilitates data transmissions between the electronic device and one or more other elements of the system (e.g., tags, dispensers, a central computer, etc.).

In one or more embodiments, the system may determine the number of steps, activities, and/or locations of one or more providers (e.g., wearing tags) on an end device, through aggregated analytics of multiple devices, or through analysis at one or more centralized computers and/or servers. In one embodiment, the system may determine, via any of the above means, activities and locations of hospital equipment (for example, hospital beds) that include a tag (as described herein). In at least one embodiment, the present systems and methods may analyze and identify patterns of interest (for example, patterns of hand hygiene activities in a particular location) based on data collected by a sensor network and data stored in the computers/servers. In one or more embodiments, the system may identify data patterns through a combination of data collected by the sensor network as well as pulled from other data sources, including, but not limited to data from a medical record system, from infection surveillance software, from other third party analytics programs, from other electronic sensors or systems, or data manually entered by facility personnel. In one embodiment, the system performs pattern recognition by leveraging a scoring algorithm, wherein multiple factors are each assigned a static or dynamic weight and, from the factors, the system calculates an aggregated metric.

In various embodiments, the systems and methods include one or more algorithms that are developed to identify and predict when potentially dangerous situations may occur. In various embodiments, the situations may include one or more of the combinations of: 1) patient with high risk organisms (MRDOs, C. Diff, MRSA, etc.) where there is an elevated risk for infections, patient with increased risk for acquiring infections (such as antibiotics, prior history, central line, etc.); 2) rooms or patients that have atypical levels of clinical/patient engagement (e.g., periods of time where clinicians do not check on the patients or very high levels of engagement); 3) situations where there is elevated risk of horizontal cross contamination (e.g., situations where individuals or groups of individual fail to perform hand hygiene and/or isolation procedures one or more times with one or more patients); and 4) situations where one or more providers fail to perform hand hygiene or isolation procedures numerous times going between numerous patients.

Thus, in one or more embodiments, the system centrally collects data from one or more dispensers, from one or more sensors of one or more tags and from memory (e.g., local, distributed or other memory included in the system), and centrally performs pattern recognition and analysis. In particular embodiments, the systems and methods include displaying, visualizing, communicating, and notifying individuals based on the results of an analysis and/or other determinations discussed herein. In some embodiments, data may be communicated through one or more mediums including, but not limited to: 1) a web dashboard; 2) e-mail; 3) text message; 4) mobile or desktop application with or without active notification; 5) phone call or message; 6) visual display in a facility; and 7) one or more mediums and/or methods for transmitting the data. In at least one embodiment, the system displays a particular associated facility's layout (e.g., the system displays the layout of an associated hospital or other medical facility) with multiple ways to view and/or display data to indicate patterns, analysis, determinations, etc. that have been detected or are occurring. As will be understood, the system may display data or patterns dynamically or statically to convey multiple types of data through a variety of display visualization techniques. In a particular embodiment, one or more dimensions of the data can be displayed through a combination of location, shape, color, size, flashing or blinking, motion, and/or a history based motion.

Figure 12:
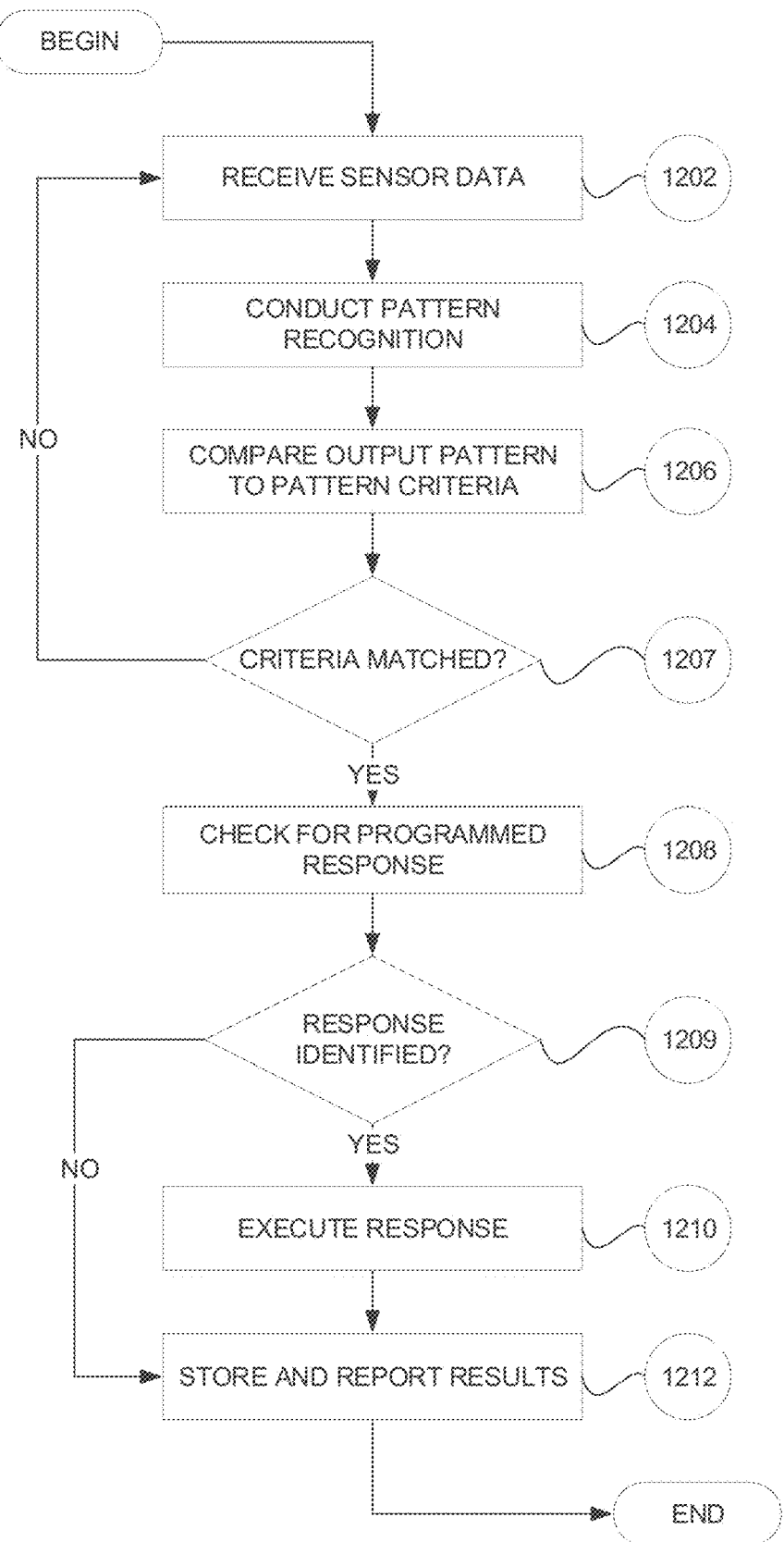
FIG. 12 is a flowchart illustrating an exemplary data collection, analysis, and response process, according to one embodiment of the present disclosure.

In various embodiments, the system uses data analytics to monitor, evaluate, and influence hand hygiene behavior. An exemplary real-time analysis and notification methodology for creating and transmitting alerts regarding potential high risk situations and for determining workflow patterns is depicted in FIG. 12 and discussed below. As will be understood by one of ordinary skill in the art, the steps and processes shown in FIG. 12 (and those of all other flowcharts and sequence diagrams shown and described herein) may operate concurrently and continuously or generally asynchronous and independently, and are not necessarily performed in the order shown. Particular embodiments may omit one or more steps of one or more flowcharts and/or sequence diagrams described herein without departing from the spirit and principles of the disclosure.

At step 1202, the system receives sensor data from one or more sources including, but not limited to: 1) a sensor network (e.g., as described herein); 2) one or more individual sensors; 3) one or more tags (as described herein); 4) one or more dispensers; and 5) one or more other data sources. In various embodiments, the sensor data may be associated with one or more of: 1) a single provider; 2) two or more providers (for example, a provider group as described herein); 3) one or more specific locations (for example, a specific hospital room, specific hallway, etc.); 4) a specific time range; 5) other parameters. In one or more embodiments, the sensor data may include, but is not limited to: 1) location information (for example a position of a specific provider in a given facility layout); 2) hygiene information (e.g., from one or more dispensers described herein); 3) movement information (e.g., from one or more tags described herein); 4) environment information, such as temperature, humidity, etc.; and 5) other sensor information. In at least one embodiment, the system may retrieve additional real time and/or historical sensor data stored in local memory, in a distributed database, or in or more other data storage locations.

In various embodiments, the system may receive sensor data automatically and/or in response to receipt of a command (e.g., from a system user). In one or more embodiments, the system may receive data continuously, at pre-determined time intervals and/or in response to one or more specific triggers. For example, the system may automatically receive data following a hand hygiene event wherein a provider failed to dispense hand hygiene agent from a dispenser within a pre-determined time interval or upon entering and/or leaving a particular patient room. In at least one embodiment, the system may identify an initial anomaly in hand hygiene behavior and automatically receive sensor data henceforth that is associated with any and all providers, dispensers, and sensors determined to be proximate to the identified initial anomaly.

For example, a provider wearing a tag may enter a patient room and pass within a predetermined proximity to a dispenser. In the same example, a proximity detector of the dispenser may detect the proximity of the provider, and a communication component of the dispenser may communicate with a transmission module of the tag and receive a provider identifier associated with the provider. Continuing with the example, if the dispenser determines that the provider failed to dispense antiseptic solution from the dispenser within a predetermined period of time after moving within the predetermined proximity of the detector, the dispenser may (substantially) automatically transmit the provider identifier and hygiene data (documenting the failure-to-dispense event) to a central computing station and/or data collection server (of the system).

In various embodiments, upon receipt of the identifier and the hygiene data, the central computing station and/or data collection server may transmit a "continuous high power" command to the transmission module (of the tag), wherein the command may be received by a tag processor. In at least one embodiment, upon receiving the command, the tag processor: 1) initializes the transmission module to continuously operate in a high power transmission mode; and 2) continuously (e.g., at regular, repeated intervals) transmits data (collected from one or more sensors) to the central computing station and/or data collection server. In one embodiment, the central computing station and/or data collection server may receive a provider location from the provider tag and transmit commands to one or more displays, one or more dispensers, and one or more tags that are determined to be proximate to the collected provider location.

In some embodiments, the commands transmitted by the system may initialize behavior changes in the one or more dispensers and/or one or more tags. For example, the commands may: 1) cause the one or more displays and one or more dispensers to generate and/or display alarms and alerts instructing the provider to dispense hand hygiene solution; and 2) cause the one or more tags to operate in a high power transmission mode and transmit their locations to the central computing station and/or data collection server. In at least one embodiment, the central computing station and/or data collection server may analyze the transmitted locations and determine if one or more other providers (or hospital equipment) have potentially come into contact with the provider that failed to dispense hand hygiene solution. In some embodiments, if the central computing station and/or data collection server determines that the one or more other providers (or hospital equipment) have potentially come into contact with the provider, one or more alerts (advising use of a dispenser) are generated and transmitted to one or more dispensers that are proximate to one or more most recently transmitted locations of the one or more other providers. Thus, in various embodiments, the system may automatically detect hand hygiene situations, continuously monitor facility assets and personnel (e.g. providers) involved in hand hygiene situations and coordinate one or more responses to detected hand hygiene situations (e.g., by transmitting alerts and commands to one or more tags, one or more dispensers and one or more providers).

At step 1204, the system performs pattern recognition to analyze the received sensor data. In one or more embodiments, the systems may perform methods including, but not limited to: 1) cluster analysis; 2) comparison to means, medians, and standard deviations/standard error; 3) linear and/or non-linear regression; 4) one or more machine learning methods. In at least one embodiment, the system, as an output of pattern recognition, defines one or more identified patterns. In various embodiments, the one or more identified patterns may be defined as one or more of numerical data, Boolean data, and other data formats suitable for performing comparison to pattern criteria (as further described herein).

At step 1206, the system compares the output of step 1204 (e.g., the one or more identified patterns) to at least one set of pattern criteria. In various embodiments, the at least one set of pattern criteria may include one or more thresholds and/or pre-defined rules. In at least one embodiment, the system determines if the output satisfies the at least one set of pattern criteria. For example, the system may determine if an identified hygiene pattern for a particular provider in a particular set of patient rooms matches criteria for a potential cross-contamination scenario. Thus, the system may receive and/or retrieve and analyze sensor data to determine if one or more pre-defined scenarios are likely to occur, are currently occurring, or have already occurred. In one or more embodiments, the system may automatically compare pattern recognition outputs to a plurality of pattern criteria sets to determine if a scenario has occurred, is currently occurring, or is likely to occur.

At step 1207, the system determines if an output pattern (of step 1204) matched at least one set of pattern criteria (in step 1206). In various embodiments, if the system determines that the output of step 1204 matches the at least one set of pattern criteria, the system proceeds to step 1208. In at least one embodiment, if the system determines that the output does not match the at least one set of pattern criteria, the system returns to step 1202 and receives additional sensor data that may be evaluated (via the steps described herein and illustrated in FIG. 12) singularly or in combination with previously received sensor data.

For example, the system may receive an identifier and data (including location data) from a tag that is affixed to a hospital bed currently occupied by a patient with C. Diff (e.g., which may be discerned when the system processes the identifier). In various embodiments, the system may perform pattern recognition on the data (and, in some embodiments, related dispenser data) and determine, based on matching criteria, that the C. Diff. hospital bed has been moved to a "clean" area of a hospital. Thus, in the same example, the system may determine that one or more patterns in the location data match criteria indicating that the C. Diff. hospital bed is in a maternity ward of a hospital, and accordingly, proceed to determine a response strategy. Alternatively, if the system determines that the one or more patterns in the location data indicate that the C. Diff. hospital bed is in an isolation ward of the hospital, the system may continue to receive data and monitor the location of the C. Diff. hospital bed. In at least one embodiment, the matching criteria may include, separately or in combination, numerical metrics, Booleans and other data formats. In the above example, the matching criteria may include, but are not limited to, a location-type data (e.g., a maternity ward location) and C. Diff. Boolean data (e.g., a C. Diff.="True" Boolean).

At step 1208, the system determines how to respond to an identified and criteria-matching pattern. In various embodiments, the system may retrieve and index a set of pre-programmed responses that address criteria-matching patterns. In at least one embodiment, the set of responses may be stored within local, distributed, or other memory (all of which may be included in the system). In one or more embodiments, the pre-programmed responses may include, but are not limited to: 1) one or more dispenser commands that (when executed by the system) modify behavior of one or more dispensers (for example, particular dispensers associated with the identified pattern); 2) one or more alert commands that (when executed by the system) cause a variety of pre-programmed notifications to be generated and delivered to one or more specific destinations (e.g., specific providers, alert displays, etc.); and 3) one or more tag commands that (when executed by the system) modify behavior of one or more tags. Thus, the system may include one or more pre-programmed responses that are each associated with specific criteria-matching patterns.

Continuing with the above example (wherein the system determines that a patient-occupied C. Diff. hospital bed is in a maternity ward of a hospital), the system may index a list of pre-programmed responses and identify a response (such as, "Hospital Bed Potential Cross-Infection Scenario") that has been programmatically associated with the identified pattern. In the same example, the identified response may include, but is not limited to: 1) generating and transmitting one or more commands to one or more dispensers and one or more displays located in the maternity ward; 2) upon receipt of one or more commands, generating alarms and alerts at the one or more dispensers and one or more displays in the maternity ward, wherein the alarms and alerts inform personnel therein that a potential cross-infection scenario has occurred and that the C. Diff. hospital bed must be moved to an isolation ward. It should be understood that the present system is not limited in its response and pattern identification capacities by any example herein. Specific scenarios and responses are provided herein for exemplary purposes, but do not place limits upon activities of the present systems and methods.

In another example, the system may recognize a particular pattern (in step 1204), wherein: 1) a provider wearing a tag entered a room containing a dispenser; 2) the provider moved within a predetermined proximity of the dispenser, whereupon a proximity detector therein detected the movement; 3) the dispenser communicated with (e.g., interrogated) a transmission module; 4) a tag transmission module transmitted to the dispenser (and a central computing station and/or data collection server) a provider identifier and sensor data from a tag processor (which was received from one or more sensors therein); 4) the dispenser determined that the provider failed to dispense antiseptic solution from the dispenser within a predetermined period of time after moving within the predetermined proximity of the proximity detector; 5) the dispenser transmitted the provider identifier, the sensor data (including location data) and other data associated with the determined hygiene failure to a central computing station and/or data collection server; 6) the tag processor, via the transmission module, transmitted additional (e.g., more recent) data to the central computing station and/or the data collection server indicating that the provider was in a new location (e.g., a different patient room from the previous room the provider entered); and 7) the central computing station and/or data collection server performed pattern recognition and determined that the provider was in a first patient room containing a patient with C. Diff. and failed to dispense antiseptic solution after entering, while occupying and after exiting the C. Diff. patient's room and has now entered a patient second room (e.g., potentially establishing a potential high-risk scenario for cross infection).

In the same example, the system may compare the pattern (in step 1206) to one or more pattern criteria and determine (in step 1207) that the pattern matches particular criteria associated with instances wherein a high-risk of spreading infection has been created. In various embodiments, the particular criteria may include, but are not limited to: 1) at least one C. Diff. Boolean (e.g., C. Diff.="True"); 2) at least one hygiene-performed Boolean (e.g., hygiene-performed="False"); and 3) two or more location-type data (e.g., "Location 1" data and "Location 2" data). Accordingly, the system may proceed (in step 1208) to determine if one or more pre-programmed responses exist (e.g., that address the identified pattern). In one or more embodiments, the system may index the one or more pre-programmed responses by providing the matched particular criteria (from steps 1206 and 1207) as an input to a response search process. Continuing with the same example, the system may identify a response that includes, but is not limited to: 1) generating and transmitting a notification (e.g. a cross-infection alert) to one or more electronic devices (in particular, an electronic device of the provider); 2) modifying one or more dispensers located near the provider to emit an alert; and 3) modifying behavior of a tag (e.g., worn by the provider) such that the tag transmits only in high-power mode for a specific time period, thus enabling increased accuracy and precision in monitoring movement of the provider.

In various embodiments, a notification transmitted by the system in as part of an executed response may include, but is not limited to, automatically and/or manually generated emails, texts, visualization (e.g., digital images, etc.), and electronic push notifications that summarize the identified hygiene pattern and response (or otherwise indicate an issue or emergency). In at least one embodiment, the notification may be transmitted to one or more computing devices including, but not limited to: 1) one or more mobile electronic devices (e.g., phones, tablets, laptops, etc.); 2) one or more computer workstations (e.g., located and/or affiliated with a facility at which the system is installed); 3) one or more visual displays; 4) one or more audio sources (e.g., public announcement ("PA") systems located throughout a facility; and 5) one or more video sources/displays (e.g., televisions, monitors, etc.) located throughout a facility. Thus, continuing with the above example, the system may: 1) generate a cross-infection audio alert (e.g., "Alert, potential cross infection event, conduct hygiene protocols immediately") and a visual alert (e.g., text or otherwise); 2) transmit the audio alert to a hospital PA system (which delivers the audio alert as an announcement); and 3) transmit the visual alert to one or more displays and one or more electronic devices (e.g., carried by providers) located within a particular proximity to the tag (e.g., of the identified provider that failed to dispense solution).

In various embodiments, the system may modify the behavior of one or more tags by transmitting a behavior command to a transmission module of each of the one or more tags (whereupon receiving the command, a tag processor processes and executes the command). As will be understood, the behavior command may include instructions for the tag to vibrate, blink, or make an audible noise. Continuing with the above example, the system may transmit a "continuous high power" command to the tag of the identified provider and to one or more tags of one or more providers and/or hospital equipment determined to be located near the identified provider. In various embodiments, a transmission module and a tag processor of the identified provider and each of the one or more persons and/or hospital equipment may receive the command and, accordingly, initialize the transmission module to continuously operate in a high power transmission mode. In at least one embodiment, execution of the behavior command may permit the system to continue to monitor locations and activities of the one or more providers and/or hospital equipment and perform additional pattern recognition processes (e.g., to monitor and, if so determined, continue to respond to the potential cross-infection event scenario). In at least one embodiment, a transmission module may operate in a continuous high power transmission mode (e.g., in response to receipt of a command) for a pre-programmed time interval, or may operate until receipt of a command which directs the transmission module to operate otherwise.

At step 1209, the system determines if a response has been identified. In various embodiments, if the system determines that a response was identified at step 1208, the system proceeds to step 1210. In at least one embodiment, if the system determines that a response was not identified at step 1208, the system proceeds immediately to step 1212.

At step 1210, the system executes the identified response. In various embodiments, the system may first a) generate and transmit a report (e.g., of the identified pattern and response) to one or more pre-defined destinations that are associated with the pattern and/or response and b) await receipt of a "proceed" command before executing the identified response. In at least one embodiment, the "proceed" command may be sourced from a system operator, a provider (for example, a supervisor), or other system modules and/or programs. In one or more embodiments, the system may automatically execute any response, or may be configured to only automatically execute specific responses. For example, the system may be configured to only automatically execute responses that are associated with specific patterns wherein a potential high-risk scenario has been established.

At step 1212, the system stores results including, but not limited to: 1) the output of step 1204 and associated pattern criteria that the system determined were satisfied by the output; 2) the response identified in 1208; and 3) details regarding execution of the identified response during step 1210. In various embodiments, the system may store the results by generating an electronic report identifying the output and the associated pattern criteria. In one or more embodiments, the electronic report may further include, but is not limited to: 1) provider information (e.g., one or more provider identifiers, etc.); 2) time information indicating a particular period of time with which the output is associated; and 3) one or more responses that were identified and executed in steps 1208 and 1210.

For example, a provider wearing a first tag may move a hospital bed (with a second tag attached therein) occupied by a patient with MRSA to a particular room. In various embodiments, the first and the second tag may, via a transmission module, transmit a first and a second identifier, as well as sensor data, to the system (e.g., to a central computing station and/or a data collection server). In one or more embodiments, the system may (e.g., at step 1202) receive the first and second identifiers and the sensor data. In at least one embodiment, the system (e.g., at step 1204) may conduct pattern recognition on the sensor data and the identifiers, and determine a particular pattern. Continuing with the same example, the system may determine a particular pattern that includes, but is not limited to: 1) location data indicating the particular room is currently occupied by the provider and/or the hospital bed (which is occupied by the patient); 2) Boolean data indicating whether or not the patient has MRSA; 3) temperature data that has been converted into a Boolean data-type (or other data type) and that indicates whether or not a temperature of the particular room may elevate potential risk of spreading, incubating, and/or complicating MRSA infection; and 4) humidity data that has been converted into a Boolean data-type (or other data type) and that indicates a humidity of the particular room may elevate potential risk of spreading, incubating, and/or complicating MRSA infection. In various embodiments, the system then (e.g., at step 1206) compares the particular pattern to one or more pattern criteria. In the same example, the system may determine that the particular pattern matches criteria including, but not limited to: 1) MRSA Boolean="True"; 2) MRSA Temperature Boolean="True"; 3) MRSA Humidity Boolean="True"; and 4) location data indicating that the bed is in the particular room and that the provider is in proximity to the particular room.

Accordingly, proceeding to step 1207, the system may determine that the particular pattern matches the criteria. Thus, in at least one embodiment, the system proceeds to step 1208 and checks for a programmed response. Continuing with the above example, the system provides the matching criteria as an input to a response indexing process. In one or more embodiments, the system determines (at step 1209) that a response has been successfully identified. In the same example, the system may proceed to step 1210 and execute the response. In at least one embodiment, execution of the response may include, but is not limited to: 1) generating and transmitting an electronic text alert to a mobile electronic device of the provider that indicates the temperature and the humidity of the particular room should be adjusted to meet specific criteria included in the text alert (for example, 68 degrees Fahrenheit and 40% humidity); 2) generating and transmitting a behavior command to the dispenser located in the particular room that, when received, causes a speaker of the dispenser to emit an audio alert (which may be similar to the text alert; and 3) generating and transmitting a behavior command to the second tag (e.g., affixed to the hospital bed) that, when received, causes the second tag to operate in a high power transmission mode (e.g., so that the system may continue to monitor the temperature and humidity of the particular room). In the same example, after executing the response, the system proceeds to step 1212 and stores, in memory, the first and second identifiers, the particular pattern, the matching criteria, the executed response, and the sensor data (used to determine the particular pattern). In at least one embodiment, the system may generate and transmit a report including, but not limited to: 1) the particular pattern; 2) the matched criteria; 3) provider and/or equipment information (e.g., the first and second identifiers, etc.); 4) time information indicating a particular period of time with which the output is associated (e.g., a time the transduced sensor data was generated at the tag processor and received by the system; and 5) one or more responses that were identified and executed in steps 1208-1210.

CONCLUSION

One should note that the flowcharts included herein show the architecture, functionality, and operation of a possible implementation of software. In this regard, each block can be interpreted to represent a module, segment, or portion of code, which comprises one or more executable instructions for implementing the specified logical function(s). It should also be noted that in some alternative implementations, the functions noted in the blocks may occur out of the order and/or not at all. For example, two blocks shown in succession may in fact be executed substantially concurrently or the blocks may sometimes be executed in the reverse order, depending upon the functionality involved.

One should note that any of the functionality described herein can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" contains, stores, communicates, propagates and/or transports the program for use by or in connection with the instruction execution system, apparatus, or device. The computer readable medium can be, for example but not limited to, an electronic, magnetic, optical, electromagnetic, infrared, or semiconductor system, apparatus, or device. More specific examples (a nonexhaustive list) of a computer-readable medium include a portable computer diskette (magnetic), a random access memory (RAM) (electronic), a read-only memory (ROM) (electronic), an erasable programmable read-only memory (EPROM or Flash memory) (electronic), and a portable compact disc read-only memory (CDROM) (optical).

It should be emphasized that the above-described embodiments are merely possible examples of implementations set forth for a clear understanding of the principles of this disclosure. Many variations and modifications may be made to the above-described embodiments without departing substantially from the spirit and principles of the disclosure. All such modifications and variations are intended to be included herein within the scope of this disclosure and protected by the accompanying claims.

We claim:

1. A hand sanitization system comprising:
   at least one sanitization unit comprising:
      a proximity detector operatively connected to a housing, the proximity detector operative to determine proximity of a person with respect to the at least one sanitization unit;
      a proximity sensor action counter operatively connected to the proximity detector, the proximity sensor action counter for counting each proximity indication from the proximity detector indicating when the person is within a particular predetermined range;
      a sanitizer action counter operatively connected to a dispenser attached to the at least one sanitization unit, the sanitizer action counter for counting each time the particular dispenser is activated;
      an alarm operatively connected to the housing and being operative to provide an indication to the person, the indication corresponding to the person failing to dispense antiseptic solution from the dispenser within a particular predetermined period of time after moving within the particular predetermined range of the at least one sanitization unit;
      an alarm counter operatively connected to the alarm, the alarm counter for counting each time the alarm is activated; and
      a sanitization unit processor operatively connected to memory and a sanitization radio frequency module for communicating with at least one tag and a central computing system;
   the at least one tag comprising a tag radio frequency module operative to communicate with the at least one sanitization unit and the central computing system; and
   the central computing system in communication with the at least one sanitization unit and the at least one tag and comprising at least one centralized processor for receiving an alert notification in response to receiving:
      a) an indication from the at least one sanitization unit that the person failed to dispense antiseptic solution from the dispenser within the particular predetermined period of time after moving within the particular predetermined range of the at least one sanitization unit; and b) an indication from the at least one tag that the at least one tag has moved beyond a predetermined distance from the particular predetermined range.

2. The hand sanitization system of claim 1, wherein:
   the at least one tag further comprises one or more sensors for tracking a location of the at least one tag; and
   the one or more sensors comprise a GPS sensor.

3. The hand sanitization system of claim 2, wherein:
   the at least one tag comprises an accelerometer; and
   the central computing system determines an approximate speed at which the at least one tag has moved beyond the predetermined distance from the particular predetermined range.

4. The hand sanitization system of claim 1, wherein:
   the at least one sanitization unit is a first sanitization unit;
   the central computing system is in communication with the first sanitization unit and the at least one tag and comprising at least one centralized processor for providing an alert in response to receiving:
      an indication from the first sanitization unit that the person failed to dispense antiseptic solution from the dispenser within the particular predetermined period of time after moving within the particular predetermined range of the first sanitization unit;
      an indication from the least one tag that the at least one tag has moved beyond a predetermined distance from the particular predetermined range, providing an alert notification to the person; and
      an indication from a second sanitization unit that the person failed to dispense antiseptic solution from a second dispenser attached to the second sanitization unit.

5. The hand sanitization system of claim 4, wherein the alert comprises a notification to a mobile device associated with the person.

6. The hand sanitization system of claim 4, wherein the alert comprises a notification to a third-party computing system.

7. The hand sanitization system of claim 4, wherein:
   the second sanitization unit comprises a second sanitization unit processor operatively connected to memory;
   the second sanitization unit processor is configured for receiving one or more properties via a network;

the one or more properties modify a behavior of the second sanitization unit; and the alert comprises the one or more properties for modifying the behavior of the second sanitization unit.

8. The hand sanitization system of claim 7, wherein the one or more properties modify the behavior of the second sanitization unit by causing the second sanitization unit to sound an audible alarm.

9. The hand sanitization system of claim 7, wherein the one or more properties modify the behavior of the second sanitization unit by causing the second sanitization unit to increase a volume of an audible notification.

10. A hand sanitization tracking method comprising:
providing an alert notification in response to receiving at a central computing system:
an indication that a person failed to dispense antiseptic solution from a dispenser within a particular predetermined period of time after moving within a particular predetermined range of at least one sanitization unit from a sanitization unit processor operatively connected to memory and a sanitization radio frequency module for communicating with at least one tag and the central computing system, wherein the at least one sanitization unit comprises:
a proximity detector operatively connected to a housing, the proximity detector operative to determine proximity of the person with respect to the at least one sanitization unit;
a proximity sensor action counter operatively connected to the proximity detector, the proximity sensor action counter for counting each proximity indication from the proximity detector indicating when the person is within the particular predetermined range;
a sanitizer action counter operatively connected to a dispenser attached to the at least one sanitization unit, the sanitizer action counter for counting each time the particular dispenser is activated;
an alarm operatively connected to the housing and being operative to provide an indication to the person, the indication corresponding to the person failing to dispense antiseptic solution from the particular dispenser within a particular predetermined period of time after moving within the particular predetermined range of the sanitization unit; and
an alarm counter operatively connected to the alarm, the alarm counter for counting each time the alarm is activated; and
an indication that at least one tag has moved beyond a predetermined distance from the particular predetermined range from a tag radio frequency module operative to communicate with the at least one sanitization unit and the central computing system.

11. The hand sanitization tracking method of claim 10, wherein:
the at least one tag further comprises one or more sensors for tracking a location of the at least one tag; and
the one or more sensors comprise a GPS sensor.

12. The hand sanitization tracking method of claim 11, wherein:
the at least one tag comprises an accelerometer; and
the central computing system determines an approximate speed at which the at least one tag has moved beyond the predetermined distance from the particular predetermined range.

13. The hand sanitization tracking method of claim 10, wherein:
the at least one sanitization unit is a first sanitization unit;
the central computing system is in communication with the first sanitization unit and the at least one tag and comprising at least one centralized processor for providing an alert in response to receiving:
an indication from the first sanitization unit that the person failed to dispense antiseptic solution from the particular dispenser within the particular predetermined period of time after moving within the particular predetermined range of the first sanitization unit;
an indication from the least one tag that the at least one tag has moved beyond a predetermined distance from the particular predetermined range, providing an alert notification to the person; and
an indication from a second sanitization unit that the person failed to dispense antiseptic solution from a second dispenser attached to the second sanitization unit.

14. The hand sanitization tracking method of claim 13, wherein the alert comprises a notification to a mobile device associated with the person.

15. The hand sanitization tracking method of claim 13, wherein the alert comprises a notification to a third-party computing system.

16. The hand sanitization tracking method of claim 13, wherein:
the second sanitization unit comprises a second sanitization unit processor operatively connected to memory;
the second sanitization unit processor is configured for receiving one or more properties via a network;
the one or more properties modify a behavior of the second sanitization unit; and
the alert comprises the one or more properties for modifying the behavior of the second sanitization unit.

17. The hand sanitization tracking method of claim 16, wherein the one or more properties modify the behavior of the second sanitization unit by causing the second sanitization unit to sound an audible alarm.

18. The hand sanitization tracking method of claim 16, wherein the one or more properties modify the behavior of the second sanitization unit by causing the second sanitization unit to increase a volume of an audible notification.

* * * * *